(12) United States Patent
Drayson et al.

(10) Patent No.: US 10,356,563 B2
(45) Date of Patent: Jul. 16, 2019

(54) TECHNOLOGY TO FACILITATE AND PROMOTE THE USE OF ENVIRONMENTALLY-FRIENDLY TRANSPORT

(71) Applicant: Drayson Technologies (Europe) Limited, London (GB)

(72) Inventors: Paul Rudd Drayson, Lypiatt Stroud Gloucestershire (GB); Manuel Pinuela Rangel, Greater London (GB)

(73) Assignee: DRAYSON TECHNOLOGIES (EUROPE) LIMITED, London (GB)

( * ) Notice: Subject to any disclaimer, the term of this patent is extended or adjusted under 35 U.S.C. 154(b) by 0 days.

(21) Appl. No.: 15/515,917

(22) PCT Filed: Sep. 25, 2015

(86) PCT No.: PCT/EP2015/072112
§ 371 (c)(1),
(2) Date: Mar. 30, 2017

(87) PCT Pub. No.: WO2016/050639
PCT Pub. Date: Apr. 7, 2016

(65) Prior Publication Data
US 2017/0311132 A1    Oct. 26, 2017

Related U.S. Application Data

(60) Provisional application No. 62/058,549, filed on Oct. 1, 2014.

(51) Int. Cl.
*G06Q 10/10* (2012.01)
*A61B 5/11* (2006.01)
(Continued)

(52) U.S. Cl.
CPC .......... *H04W 4/046* (2013.01); *A61B 5/1123* (2013.01); *A61B 5/681* (2013.01);
(Continued)

(58) Field of Classification Search
CPC ...... G06Q 10/10; G06Q 30/0232; A61B 5/11; A61B 5/00; H04W 4/046
(Continued)

(56) References Cited

U.S. PATENT DOCUMENTS

| 9,819,754 B2* | 11/2017 | Park | A61B 5/0002 |
| 2012/0083716 A1* | 4/2012 | Yuen | A61B 5/0002 600/595 |
| 2014/0275850 A1* | 9/2014 | Venkatraman | A61B 5/0002 600/301 |

OTHER PUBLICATIONS

International Search Report and Written Opinion for corresponding PCT Application No. PCT/EP2015/072112.

\* cited by examiner

*Primary Examiner* — Tan Q Nguyen
(74) *Attorney, Agent, or Firm* — Tarolli, Sundheim, Covell & Tummino LLP

(57) ABSTRACT

The present invention provides a portable processing device comprising a journey type determining module, a journey length determining module and a communication module. The journey type determining module is operable to determine whether a journey undertaken by a person carrying the portable processing device is an environmentally-friendly journey comprising a journey undertaken in an environmentally-friendly vehicle, a journey undertaken using self-propelled means or a journey undertaken on foot. The journey length determining module is operable to determine a length of a said environmentally-friendly journey undertaken by the person carrying the portable processing device. The communication module is operable to transmit journey data
(Continued)

to record management apparatus defining the length of the environmentally-friendly journey undertaken by the person carrying the portable processing device.

19 Claims, 22 Drawing Sheets

(51) Int. Cl.
*H04W 4/04* (2009.01)
*A61B 5/00* (2006.01)
*G06F 19/00* (2018.01)
*G06F 16/23* (2019.01)
*G06Q 30/02* (2012.01)

(52) U.S. Cl.
CPC ......... *G06F 19/3481* (2013.01); *G06Q 10/10* (2013.01); *A61B 2560/0242* (2013.01); *G06F 16/23* (2019.01); *G06Q 30/0233* (2013.01); *Y02A 90/26* (2018.01)

(58) Field of Classification Search
USPC ........................................................ 701/519
See application file for complete search history.

TRANSMIT SIGNALS IDENTIFYING THE VEHICLE AS AN ENVIRONMENTALLY-FRIENDLY VEHICLE TO A PORTABLE PROCESSING DEVICE OF A PERSON IN THE VEHICLE — S18-2

TECHNOLOGY TO FACILITATE AND PROMOTE THE USE OF ENVIRONMENTALLY-FRIENDLY TRANSPORT

RELATED APPLICATION

This present application is a U.S. National Stage Application under 35 USC 371, claiming priority to PCT Application No. PCT/EP2015/072112, filed on Sep. 25, 2015; which claims priority from US Provisional Patent Application No. 62/058,549, filed on Oct. 1, 2014, the entirety of both of which are incorporated herein by reference.

FIELD OF THE INVENTION

The present invention relates to technology to facilitate and promote the use of environmentally-friendly transport to improve air quality and human health.

BACKGROUND

Different modes of environmentally-friendly and health improving transport are currently available and new modes of environmentally-friendly transport are under development. There is a growing need to use this form of transport in order to reduce emissions which are harmful to human health and the environment and which can contribute to, inter alia, heart, lung disease and global warming.

Accordingly, technology is needed to facilitate and promote the use of healthy, environmentally-friendly transport over other non-environmentally-friendly modes of transport which damage human health.

SUMMARY

The present invention provides a portable processing device comprising a journey type determining module, a journey length determining module and a communication module. The journey type determining module is operable to determine whether a journey undertaken by a person carrying the portable processing device is an environmentally-friendly journey comprising a journey undertaken in an environmentally-friendly vehicle, a journey undertaken using self-propelled means or a journey undertaken on foot. The journey length determining module is operable to determine a length of a said environmentally-friendly journey undertaken by the person carrying the portable processing device. The communication module is operable to transmit journey data to record management apparatus defining the length of the environmentally-friendly journey undertaken by the person carrying the portable processing device.

The present invention also provides an identification device for an environmentally-friendly vehicle, the identification device comprising an identity providing module. The identity providing module is operable to transmit signals identifying the vehicle as an environmentally-friendly vehicle to a portable processing device of a person in the vehicle.

The present invention also provides an identification device for self-propelled means, the identification device comprising an identity providing module. The identity providing module is operable to transmit signals identifying the self-propelled means as self-propelled means to a portable processing device of a person using the self-propelled means.

The present invention also provides a processing device for mounting in an environmentally-friendly vehicle, the processing device comprising an identity receiving module, a journey length determining module and a communication module. The identity receiving module is operable to receive identifying data from at least one of a portable processing device and a card carrying identifying data of a person in the environmentally-friendly vehicle. The journey length determining module is operable to determine, for each person for which identifying data is received, a length of a journey undertaken by the person in the environmentally-friendly vehicle. The communication module is operable to transmit data to record management apparatus defining, for each person for which identifying data is received, the identifying data received by the identity receiving module and the determined length of the journey undertaken by the person in the environmentally-friendly vehicle.

The present invention also provides a processing device for mounting on self-propelled means, the processing device comprising an identity receiving module, a journey length determining module and a communication module. The identity receiving module is operable to receive identifying data from at least one of a portable processing device and a card carrying identifying data of a person using the self-propelled means. The journey length determining module is operable to determine, for each person for which identifying data is received, a length of a journey undertaken by the person using the self-propelled means. The communication module is operable to transmit data to record management apparatus defining, for each person for which identifying data is received, the identifying data received by the identity receiving module and the determined length of the journey undertaken by the person using the self-propelled means.

The present invention also provides record management apparatus configured to store and process data defining environmentally-friendly journeys undertaken by people. The record management apparatus comprises a data receiving module, a data store and a reward module. The data receiving module is operable to receive journey data defining the lengths of environmentally-friendly journeys undertaken by people. The data store is configured to store data defining, for each person, the length of environmentally-friendly journeys undertaken by the person. The reward module is operable to make available to each person a reward in dependence upon the length of environmentally-friendly journeys undertaken by the person.

The present invention also provides a method performed by a portable processing device. The method comprises determining whether a journey undertaken by a person carrying the portable processing device is an environmentally-friendly journey comprising a journey undertaken in an environmentally-friendly vehicle, a journey undertaken using self-propelled means or a journey undertaken on foot. In the event that it is determined that a journey is an environmentally-friendly journey, a length is determined of the environmentally-friendly journey undertaken by the person carrying the portable processing device and journey data is transmitted to record management apparatus defining the length of the environmentally-friendly journey undertaken by the person carrying the portable processing device.

The present invention also provides a method performed by an identification device in an environmentally-friendly vehicle. The method comprises transmitting signals identifying the vehicle as an environmentally-friendly vehicle to a portable processing device of a person in the vehicle.

The present invention also provides a method performed by an identification device on self-propelled means. The method comprises transmitting signals identifying the self-propelled means as self-propelled means to a portable processing device of a person using the self-propelled means.

The present invention also provides a method performed by a processing device in an environmentally-friendly vehicle. The method comprises receiving identifying data from at least one of a portable processing device and a card carrying identifying data of a person in the environmentally-friendly vehicle. The method further comprises determining, for each person for which identifying data is received, a length of a journey undertaken by the person in the environmentally-friendly vehicle. The method further comprises transmitting data to record management apparatus defining, for each person for which identifying data is received, the received identifying data and the determined length of the journey undertaken by the person in the environmentally-friendly vehicle.

The present invention also provides a method performed by a processing device mounted on self-propelled means. The method comprises receiving identifying data from at least one of a portable processing device and a card carrying identifying data of a person using the self-propelled means. The method further comprises determining, for each person for which identifying data is received, a length of a journey undertaken by the person using the self-propelled means. The method further comprises transmitting data to record management apparatus defining, for each person for which identifying data is received, the received identifying data and the determined length of the journey undertaken by the person using the self-propelled means.

The present invention also provides a method performed by record management apparatus which stores data defining environmentally-friendly journeys undertaken by people. The method comprises receiving journey data defining the lengths of environmentally-friendly journeys undertaken by people. The method further comprises storing data defining, for each person, the length of environmentally-friendly journeys undertaken by the person. The method further comprises making available to each person a reward in dependence upon the length of environmentally-friendly journeys undertaken by the person.

The present invention also provides a non-transitory storage medium storing computer program instructions which, when executed, cause a programmable processing apparatus to determine whether a journey undertaken by a person carrying the processing apparatus is an environmentally-friendly journey comprising a journey undertaken in an environmentally-friendly vehicle, a journey undertaken using self-propelled means or a journey undertaken on foot. In the event that it is determined that a journey is an environmentally-friendly journey, the computer program instructions, when executed, further cause the programmable processing apparatus to determine a length of the environmentally-friendly journey undertaken by the person carrying the processing apparatus, and transmit data to record management apparatus defining the length of the environmentally-friendly journey undertaken by the person carrying the processing apparatus.

The present invention also provides a non-transitory storage medium storing computer program instructions which, when executed, cause a programmable processing apparatus to receive identifying data from at least one of a portable processing device and a card carrying identifying data of a person in an environmentally-friendly vehicle. The computer program instructions, when executed, further cause the programmable processing apparatus to determine, for each person for which identifying data is received, a length of a journey undertaken by the person in the environmentally-friendly vehicle. The computer program instructions, when executed, further cause the programmable processing apparatus to transmit data to record management apparatus defining, for each person for which identifying data is received, the received identifying data and the determined length of the journey undertaken by the person in the environmentally-friendly vehicle.

The present invention also provides a non-transitory storage medium storing computer program instructions which, when executed, cause a programmable processing apparatus to receive identifying data from at least one of a portable processing device and a card carrying identifying data of a person using self-propelled means. The computer program instructions, when executed, further cause the programmable processing apparatus to determine, for each person for which identifying data is received, a length of a journey undertaken by the person using the self-propelled means. The computer program instructions, when executed, further cause the programmable processing apparatus to transmit data to record management apparatus defining, for each person for which identifying data is received, the received identifying data and the determined length of the journey undertaken by the person using the self-propelled means.

The present invention also provides a non-transitory storage medium storing computer program instructions which, when executed, cause a programmable processing apparatus to receive journey data defining the lengths of environmentally-friendly journeys undertaken by people. The computer program instructions, when executed, further cause the programmable processing apparatus to store data defining, for each person, the length of environmentally-friendly journeys undertaken by the person. The computer program instructions, when executed, further cause the programmable processing apparatus to make available to each person a reward in dependence upon the length of environmentally-friendly journeys undertaken by the person.

The present invention also provides a signal carrying computer program instructions which, when executed, cause a programmable processing apparatus to perform a method as set out above.

BRIEF DESCRIPTION OF THE DRAWINGS

Embodiments of the invention will now be described, by way of non-limiting example only, with reference to the accompanying drawings, in which:

FIG. 18 shows processing operations performed by an identification device in embodiments.

DETAILED DESCRIPTION

[Embodiment 1]

Figure 1:
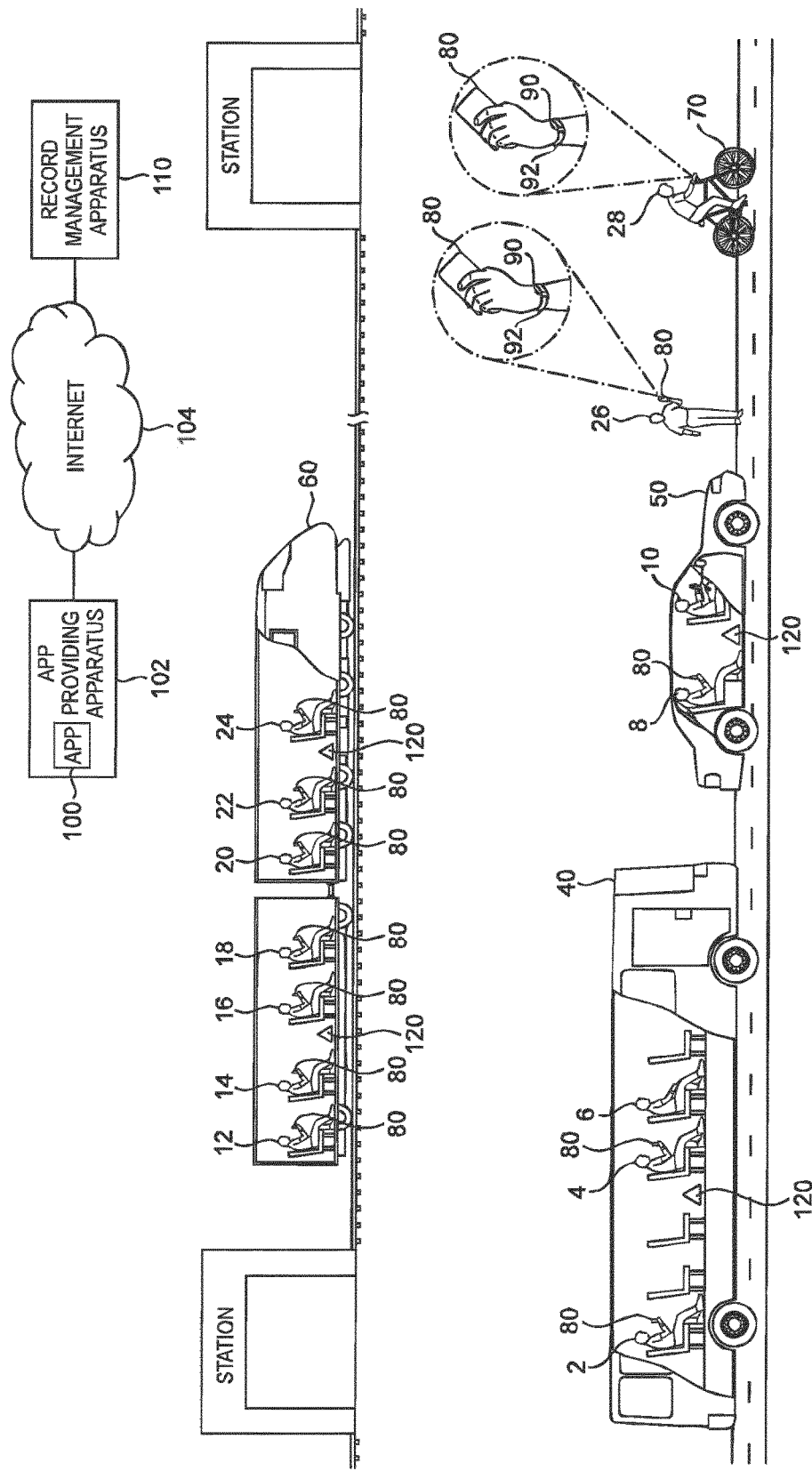
FIG. 1 semantically illustrates technology that is employed in a first embodiment when a plurality of people undertake journeys using different modes of environmentally-friendly transport.

Referring to FIG. 1, a plurality of people 2-28 undertake journeys using different modes of transport. More particularly, in the example of FIG. 1, the people 2, 4, 6 make respective journeys on a bus 40, the people 8, 10 undertake a journey in a car 50, the people 12-24 make respective journeys on a train 60, the person 26 undertakes a journey on foot, and the person 28 undertakes a journey on self-propelled means comprising a bicycle.

As will be explained in more detail below, technology is provided to incentivise people to undertake journeys using environmentally-friendly modes of transport by determining the length of each journey undertaken by a person using an environmentally-friendly mode of transport and providing rewards in dependence upon the lengths of the journeys.

It will, of course, be appreciated that the technology can be applied to environmentally-friendly modes of transport other than those shown FIG. 1. For example, the technology can be applied to vehicles such as taxis, trams, monorail trains, underground trains, motorcycles, mopeds, boats, etc.

Similarly, the technology can be applied to other self-propelled means such as scooters, skateboards, roller-skates, rollerblades, etc.

In the present embodiment, each person carries a portable processing device 80 with them each on each journey (this portable processing device 80 being visible for some, but not all of the people in FIG. 1 as some of the people may carry the portable processing device in a pocket or bag such that it is obscured from view). The portable processing device 80 may comprise a mobile telephone, smart watch, tablet computer, e-book reader or any other form of portable computer processing apparatus. Each portable processing device may comprise multiple separate parts configured to communicate with each other or may comprise one self-contained unit.

Optionally, in some cases (as illustrated for the people 26, in FIG. 1 by way of example) a person undertaking a journey may also carry one or more air quality sensors 90 for measuring one or more air quality parameters. In the example of FIG. 1, the air quality sensors 90 are shown as being carried on bracelets 92 by the people 26, 28, although they could be carried in different ways instead.

The air quality sensor(s) 90 can be powered by conventional non-rechargeable batteries, which are replaced when the batteries are empty. Alternatively, the air quality sensor(s) can be powered using energy harvesting/scavenging techniques, for example by harvesting ambient background radio-frequency (RF) energy using techniques such as those disclosed in co-pending patent applications GB 1314307.8 and PCT/GB2014/052431, the full contents of which are incorporated herein by cross-reference, or by gathering kinetic, thermal, solar, wind, and/or chemical gradient energy. As a further alternative, one or more rechargeable batteries could be provided for the air quality sensor(s) and the battery or batteries could be recharged using inductive power transfer, for example using techniques disclosed in copending patent applications GB 1215152.8, GB 1309691.2, GB 1321267.5, PCT/GB2013/051456, PCT/GB/2014/051656, CA 2817288 and MX/A/2013/006253, the full contents of which are incorporated herein by cross-reference, or by using acoustic waves (ultrasound) or optical power, such as lasers.

Each portable processing device 80 has stored therein an app 100 downloaded from an app providing apparatus 102 for example via the internet 104 or provided pre-installed by the manufacturer of the portable processing device. The app 100 comprises computer programming instructions which, when executed, cause the portable processing device 80 to perform processing as described below to determine whether a journey undertaken by the person carrying the portable processing device is an environmentally-friendly journey, to determine the length of each environmentally-friendly journey undertaken by the person, and to transmit data to record management apparatus 110 defining the lengths of the environmentally-friendly journeys undertaken by the person.

Record management apparatus 110 stores data defining, for each person, the length of environmentally-friendly journeys undertaken by that person, and furthermore makes available rewards in dependence upon the length of environmentally-friendly journeys undertaken.

Each environmentally-friendly vehicle in which a person may undertake a journey is provided with one or more identification devices 120. Each identification device 120 transmits signals which are detected by the portable processing device 80 of each person travelling in the vehicle and which identify the vehicle as an environmentally-friendly vehicle to the portable processing device 80. A vehicle may be categorised as an environmentally-friendly vehicle (and therefore be eligible to have an identification device 120 fitted thereto) in a number of different ways. For example, a vehicle may be categorised as an environmentally-friendly vehicle if its emissions are below environmental emission standards set, for example, by an authoritative organisation. In addition or instead, all or a predetermined amount of a vehicle's energy may need to be derived from renewable energy sources in order for the vehicle to be categorised as an environmentally-friendly vehicle. An authoritative organisation may be tasked with validating and certifying that vehicles meet the necessary environmentally-friendly standards and authorising the fitting of an identification device 120.

Each identification device 120 may be fitted to the environmentally-friendly vehicle during original manufacture or retro-fitted. Each identification device 120 can be powered by connecting it to the power supply of the environmentally-friendly vehicle in which it is fitted. In addition or instead, each identification device 120 can be powered with conventional non-rechargeable batteries, which are replaced when the batteries are empty. Alternatively, each identification device 120 can be powered using energy harvesting/scavenging techniques, for example by harvesting ambient background radio-frequency (RF) energy using techniques such as those disclosed in co-pending patent applications GB 1314307.8 and PCT/GB2014/052431, the full contents of which are incorporated herein by cross-reference, or by gathering kinetic, thermal, solar, wind, and/or chemical gradient energy. As a further alternative, one or more rechargeable batteries could be provided for each identification device 120 and the battery or batteries could be recharged using inductive power transfer, for example using techniques disclosed in copending patent applications GB 1215152.8, GB 1309691.2, GB 1321267.5, PCT/GB2013/051456, PCT/GB/2014/051656, CA 2817288 and MX/A/2013/006253, the full contents of which are incorporated herein by cross-reference, or by using acoustic waves (ultrasound) or optical power, such as lasers.

The technical components illustrated in FIG. 1 and the processing operations performed thereby will now be described in more detail.

Figure 2:
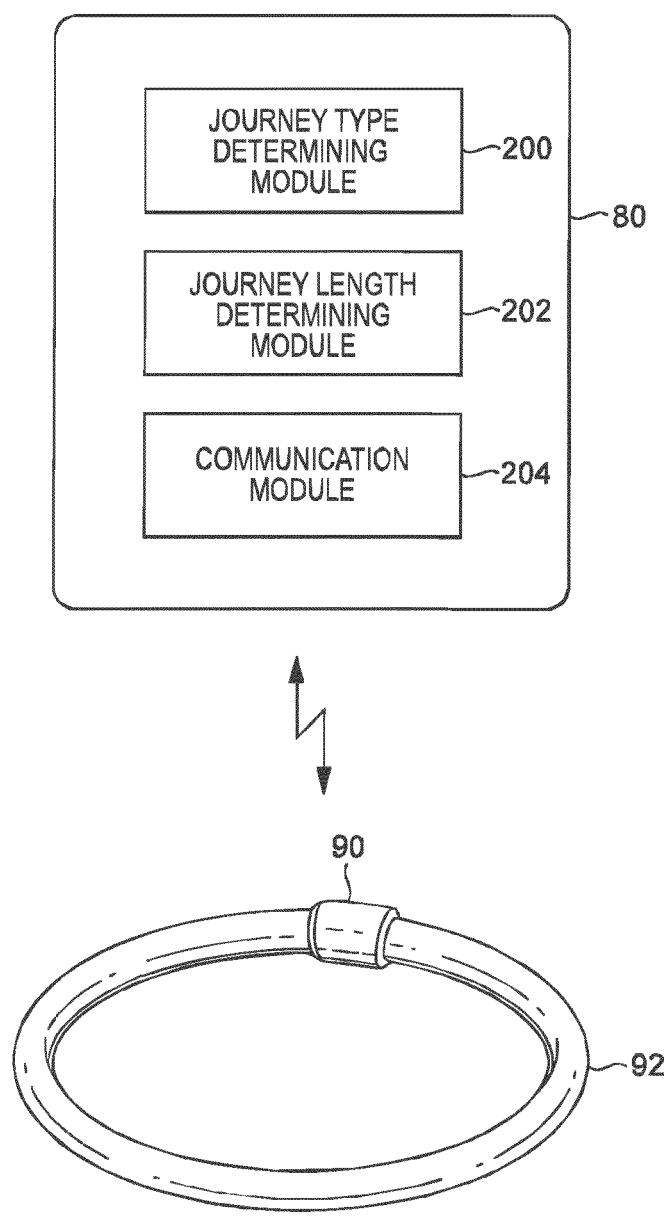
FIG. 2 semantically illustrates the functional processing modules of a portable processing device in the first embodiment carried by each person undertaking a journey, as well as the optional air quality sensor(s) that may also be carried by the person.

FIG. 2 semantically illustrates the portable processing device 80 carried by each person undertaking a journey and the optional air quality sensor(s) 90.

Referring to FIG. 2, when the processor(s) of the portable processing device 80 executes the computer program instructions of the app 100, the portable processing device 80 becomes configured to provide a number of different notional functional processing modules which, in this embodiment, comprise journey type determining module 200, journey length determining module 202 and communication module 204.

Journey length determining module 200 is operable to determine whether a journey undertaken by a person carrying the portable processing device 80 is an environmentally-friendly journey comprising a journey undertaken in an environmentally-friendly vehicle. In this embodiment, journey type determining module 200 is configured to determine if a journey is undertaken in an environmentally-friendly vehicle by detecting a characteristic signal transmitted by an identification device 120 carried in an environmentally-friendly vehicle. However, journey type determining module 200 may be configured to determine if a journey is a journey in an environmentally-friendly vehicle in different ways instead. For example, the operator or owner of an environmentally-friendly vehicle may be provided with a time-dependent code (for example a code transmitted from record management apparatus 110 that changes each predetermined unit of time, such as every minute) and a person travelling in the environmentally-friendly vehicle may be provided with this code to enter manually into his/her portable processing device using a keypad, touch-sensitive screen or other input device.

Optionally, journey type determining module 200 is operable to determine whether a journey undertaken by a person carrying the portable processing device is an environmentally-friendly journey comprising a journey undertaken on foot or an environmentally-friendly journey comprising a journey undertaken using self-propelled means. Journey type determining module 200 may be configured to determine if a journey is undertaken on foot or on self-propelled means in dependence upon at least one of speed during the journey, acceleration during the journey and vibrations during the journey.

Journey length determining module 202 is operable to determine the length of each environmentally-friendly journey undertaken by a person carrying the portable processing device 80. For example, journey length determining module 202 may be configured to determine the positions of points (such as positions determined by GPS or other means) throughout the journey and to determine the distance between the points, thereby determining the total length of the journey.

Communication module 204 is operable to transmit journey data to record management apparatus 110 defining the length of each environmentally-friendly journey undertaken by the person carrying the portable processing device 80. Each portable processing device 80 may identify itself to record management apparatus 110 during the communication so that record management apparatus 110 can identify the owner of the portable processing device 80 using a previous registration made by the person with record management apparatus 110 which associates their personal details with the ID of the portable processing apparatus 80. Alternatively, communication module 204 may be configured to transmit to record management apparatus 110 a personal ID entered by the person carrying the portable processing device for example using an input keypad, touch-sensitive screen or other input device.

Optionally, communication module 204 may be operable to transmit vehicle data to record management apparatus 110 defining at least one of the operator of the environmentally-friendly vehicle and the environmentally-friendly vehicle itself in which the environmentally-friendly journey was undertaken. Such vehicle data may be obtained by portable processing device 80 for example by receiving vehicle data transmitted by an identification device 120 in the environmentally-friendly vehicle.

Optionally, portable processing device 80 may also be operable to receive signals, for example by Bluetooth or other short-range communication technique, from one or more air quality sensors 90 carried by the person. In such a case, communication module 204 is further operable to transmit air quality measurement data received from the air quality sensor(s) to the record management apparatus.

Transmissions made by communication module 204 to record management apparatus 110 may be made in any appropriate way, for example, using a cellular network or using Wi-Fi when the portable processing device 80 is within range of a Wi-Fi router.

Portable processing device 80 may optionally be further operable to receive air quality data from record management apparatus 110 and to provide the air quality data to the person carrying the portable processing device, for example by displaying the data on a display. Thus, for example, a user of a portable processing device 80 may request and receive air quality data from record management apparatus 110 for a journey that they are about to undertake, thereby allowing them to plan their journey to avoid areas of high air pollution.

Figure 3:
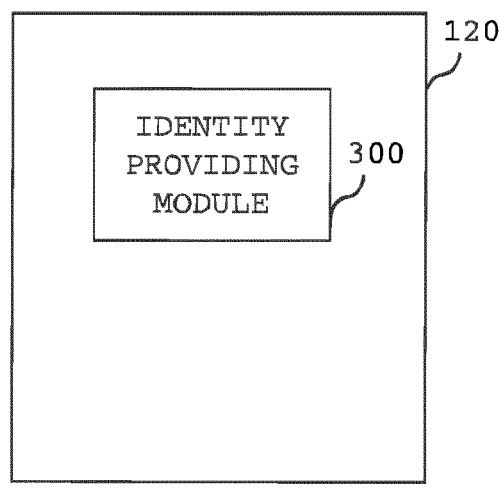
FIG. 3 shows the functional processing modules of each identification device provided in an environmentally-friendly vehicle in the first embodiment.

FIG. 3 shows the functional processing modules of identification device 120 provided in each environmentally-friendly vehicle. Identification device 120 may comprise multiple separate parts configured to communicate with each other or a single apparatus.

Referring to FIG. 3, identification device 120 comprises an identity providing module 300 that is operable to transmit signals identifying the vehicle as an environmentally-friendly vehicle so that the signals can be received by the portable processing devices 80 of people travelling in the environmentally-friendly vehicle. Optionally, the identity providing module 300 is further operable to transmit signals identifying at least one of the operator of the environmentally-friendly vehicle and the environmentally-friendly vehicle itself. The operator may be, for example, the organisation which owns the fleet of vehicles to which the environmentally-friendly vehicle belongs (such as the bus company which operates bus 40 or the train company which operates train 60 in the example of FIG. 1).

Signals transmitted by identity providing module 300 may be transmitted using Bluetooth or any other short-range transmission technique.

Figure 4:
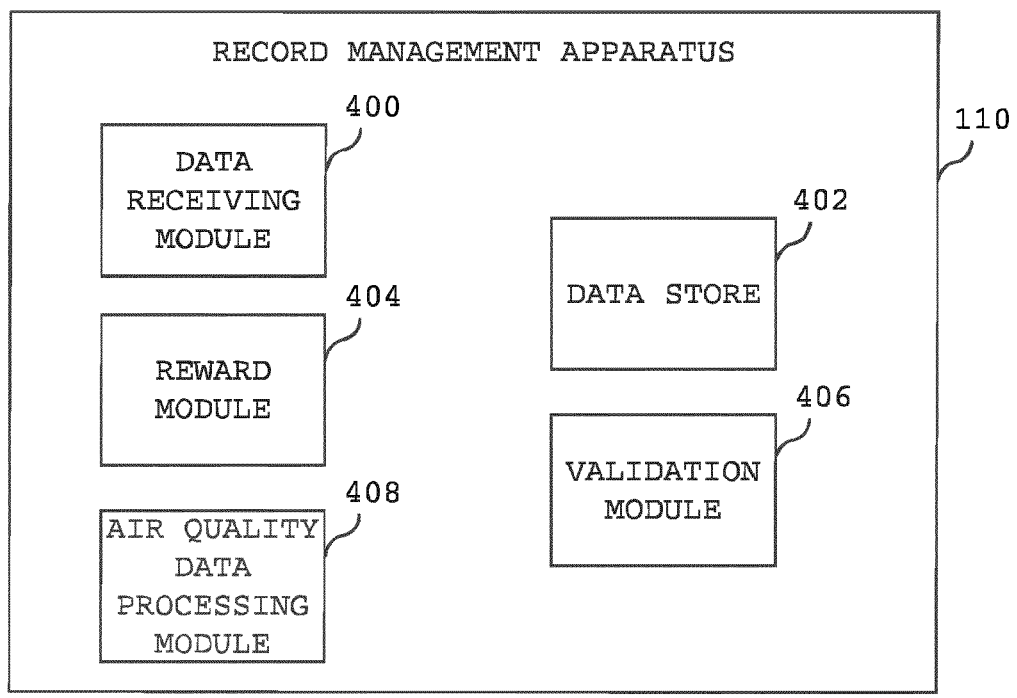
FIG. 4 shows the functional processing modules of record management apparatus in the first embodiment.

FIG. 4 shows the functional processing modules of record management apparatus 110.

Record management apparatus 110 may comprise multiple separate parts configured to communicate with each other or a single apparatus. Record management apparatus 110 may be a cloud-based server apparatus, for example.

Referring to FIG. 4, record management apparatus 110 comprises data receiving module 400, data store 402 and reward module 404. Optionally, record management apparatus 110 may further comprise validation module 406 and air quality data processing module 408.

Data receiving module 400 is operable to receive journey data defining the lengths of environmentally-friendly journeys undertaken by people. Optionally, data receiving module 400 may be further operable to receive data defining at least one of the operator of an environmentally-friendly vehicle and the environmentally-friendly vehicle itself in which an environmentally-friendly journey was undertaken. Data receiving module 400 may receive the data, for example, from portable processing devices 80 via one or more networks.

Data store 402 is configured to store data defining, for each person, the length of environmentally-friendly journeys undertaken by the person. Optionally, data store 402 is further configured to store data defining, for each operator of an environmentally-friendly vehicle, the length of environmentally-friendly journeys undertaken by people in environmentally-friendly vehicles operated by the operator. If data is received defining an environmentally-friendly vehicle itself, record management apparatus 110 may be configured to determine the operator of the environmentally-friendly vehicle using a registration made by each operator with record management apparatus 110 which identifies each of the environmentally-friendly vehicles operated by the operator.

Reward module 404 is operable to make available to each person a reward in dependence upon the length of environmentally-friendly journeys undertaken by the person. Optionally, reward module 404 is further operable to make available a reward to each operator of at least one environmentally-friendly vehicle in dependence upon the length of environmentally-friendly journeys undertaken by people in the operator's environmentally-friendly vehicle(s).

Optional validation module 406 is operable to compare journey data received from different portable processing devices 80 to determine if the different portable processing devices were carried by the same person on the same environmentally-friendly journey. Validation module 406 is therefore operable to identify fraudulent journeys, for example in which a single person carried portable processing devices belonging to a plurality of different people so that each of those different people would be credited with the length of the environmentally-friendly journey even though the journey was undertaken only by the single person. Validation module 406 may be configured to determine if different processing devices 80 were carried by the same person on the same journey by comparing at least one of position data, acceleration data and vibration data received from the different portable processing devices 80. For example, if the compared data indicates that different portable processing devices 80 were at the same positions at the same times and underwent the same accelerations at the same times and/or the same vibrations at the same times, then validation module 406 may be configured to determine that the different portable processing devices were being carried by the same person.

Optional air quality data processing module 408 is configured to receive air quality measurement data, for example any air quality measurement data transmitted by portable processing devices 80 and to make this data available for receipt by users of portable processing devices 80. This could offer, for example, an analysis feature, which enables a person to track the aggregate level of air pollution during a journey, during the day, week or year or to be advised of the least polluted route to take for a journey being planned. The app 100 can also be programmed to warn the person if they are currently travelling in an area subject to dangerously high levels of air pollution (i.e. breaching WHO limits) and to recommend an alternative route or means of transport if one exists.

Having described the functional components of the different apparatus shown in FIG. 1, the processing operations performed by those components will now be described.

Figure 5A:
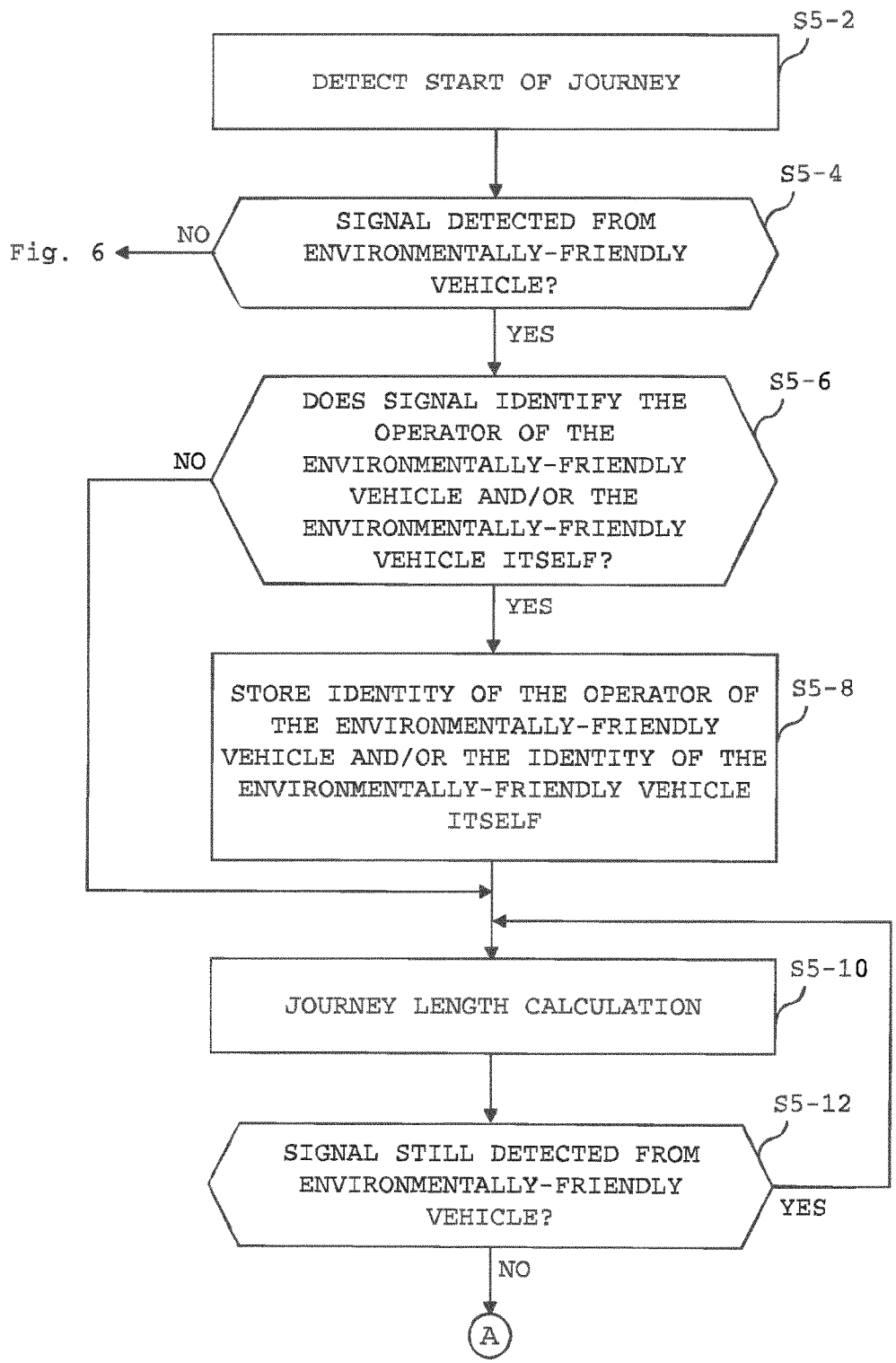
FIGS. 5a and 5b show the processing operations performed by a portable processing device when a person carrying the portable processing device undertakes a journey in the first embodiment.
Figure 5B:
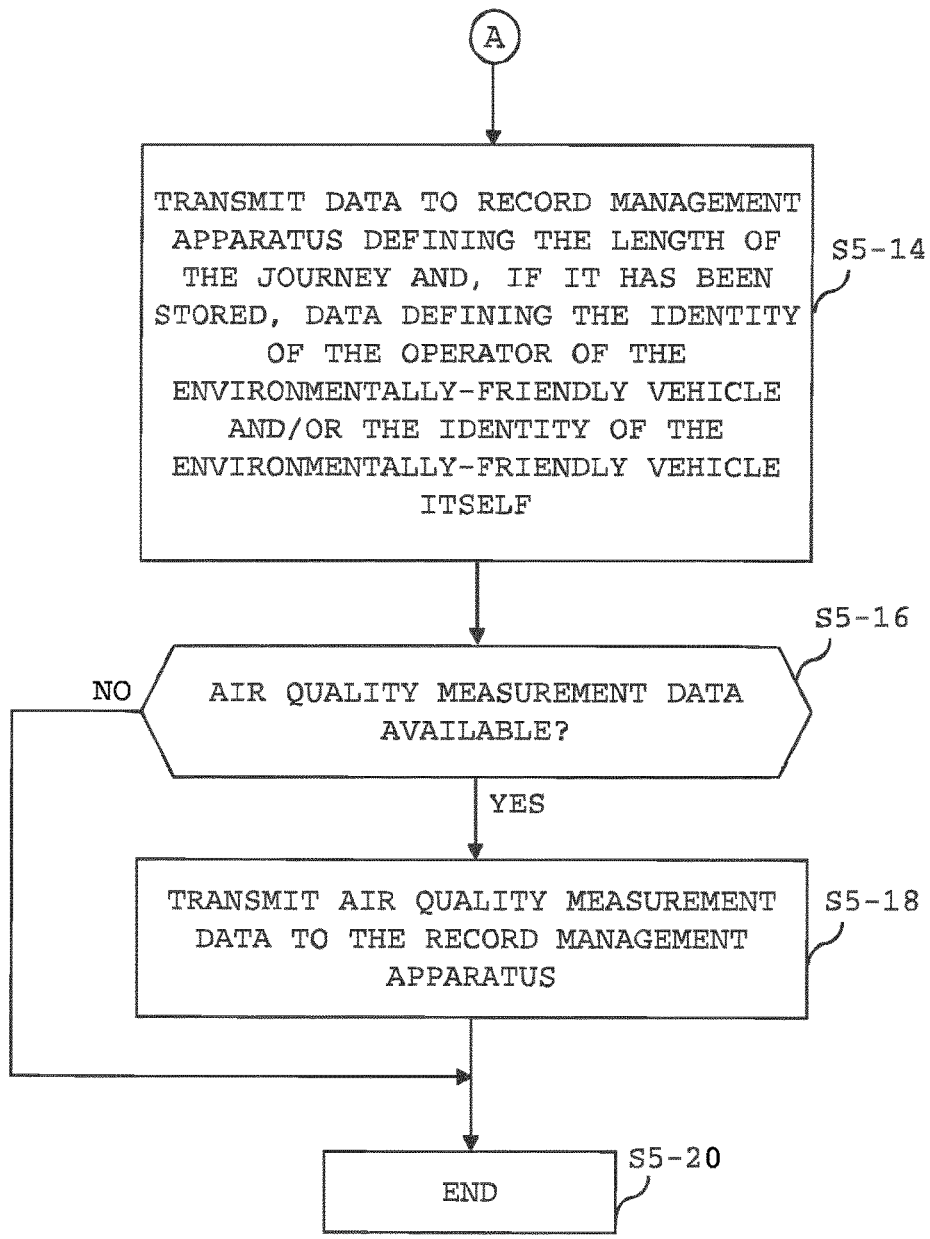

FIGS. 5a and 5b show the processing operations performed by a portable processing device 80 when a person carrying the portable processing device undertakes a journey.

At step S5-2, portable processing device 80 detects the start of the journey. This detection may be achieved in many different ways. By way of example, motion sensors in the portable processing device 80 may detect movement that has lasted for more than a predetermined duration of time and/or more than a predetermined distance. By way of further example, the start of the journey may be detected by the person carrying the portable processing device 80 providing an input using a keypad, touch-sensitive screen or other input device.

At step S5-4, a determination is made as to whether a signal from an identification device 120 in an environmentally-friendly vehicle has been received by the portable processing device 80. As noted previously, an identification device 120 emits a characteristic signal that portable processing device 80 is configured to detect and distinguish from other types of received signals.

If it is determined at step S5-4 that a signal from an identification device 120 in an environmentally-friendly vehicle has not been received, then processing proceeds to FIG. 6, which will be described later.

On the other hand, if it is determined at step S5-4 that a signal from an identification device 120 in an environmentally-friendly vehicle has been received, then processing proceeds to step S5-6, at which the signal received from identification device 120 is processed to determine whether it additionally identifies the operator of the environmentally-friendly vehicle and/or the environmentally-friendly vehicle itself.

If it is determined at step S5-6 that the signal does additionally identify the operator of the environmentally-friendly vehicle and/or the environmentally-friendly vehicle itself, then processing proceeds to step S5-8, at which portable processing device 80 stores the identity of the operator and/or the identity of the environmentally-friendly vehicle itself. On the other hand, if it determined at step S5-6 that no additional identification is provided by the received signal, then the processing at step S5-8 is omitted.

At steps S5-10 and S5-12, processing is performed to calculate the length of the journey which the person carrying the portable processing device 80 undertakes on the environmentally-friendly vehicle. More particularly, steps S5-10 and S5-12 are repeatedly performed so that the journey length calculation at step S5-10 is updated for the duration of the time for which the portable processing device 80 continues to receive the signal from the identification device 120 in the environmentally-friendly vehicle (this being checked at step S5-12). As noted previously, the signal transmitted by identification device 120 is a short-range signal. This signal is therefore received and detected by portable processing device 80 when the person carrying the portable processing device is inside the environmentally-friendly vehicle, but the signal is no longer received when the person exits the environmentally-friendly vehicle because the portable processing device 80 is quickly out-of-range of the signal from the identification device 120 (with this being detected at step S5-12).

At step S5-14, portable processing device 80 transmits data to record management apparatus 110 defining the length of the journey undertaken by the person carrying the portable processing device in the environmentally-friendly vehicle. Furthermore, if data has been stored at step S5-8 defining the operator of the environmentally-friendly vehicle and/or the identity of the environmentally-friendly vehicle itself, portable processing device 80 transmits this data as well to record management apparatus 110. The transmission of data at step S5-14 may be performed as soon as the journey has been completed, for example by transmitting the data using a cellular network. Alternatively, the transmission at step S5-14 may be delayed until a later time and transmitted, for example, using Wi-Fi when portable processing device 80 is in range of a Wi-Fi router.

At step S5-16, a determination is made as to whether portable processing device 80 has received any air quality measurement data from one or more air quality sensors 90 carried by the person.

If it is determined at step S5-16 that air quality measurement data has been received, the processing proceeds to step S5-18, at which portable processing device 80 transmits the air quality measurement data to record management apparatus 110. The transmission of air quality measurement data at step S5-18 may be performed throughout the journey while the journey is continuing, as soon as the journey has finished, or at a delayed time thereafter. On the other hand, if it determined at step S5-16 that no air quality measurement data has been received, then the processing at step S5-18 is omitted.

Processing ends at step S5-20 and portable processing device enters a stand-by mode to await the start of the next journey.

Figure 6:
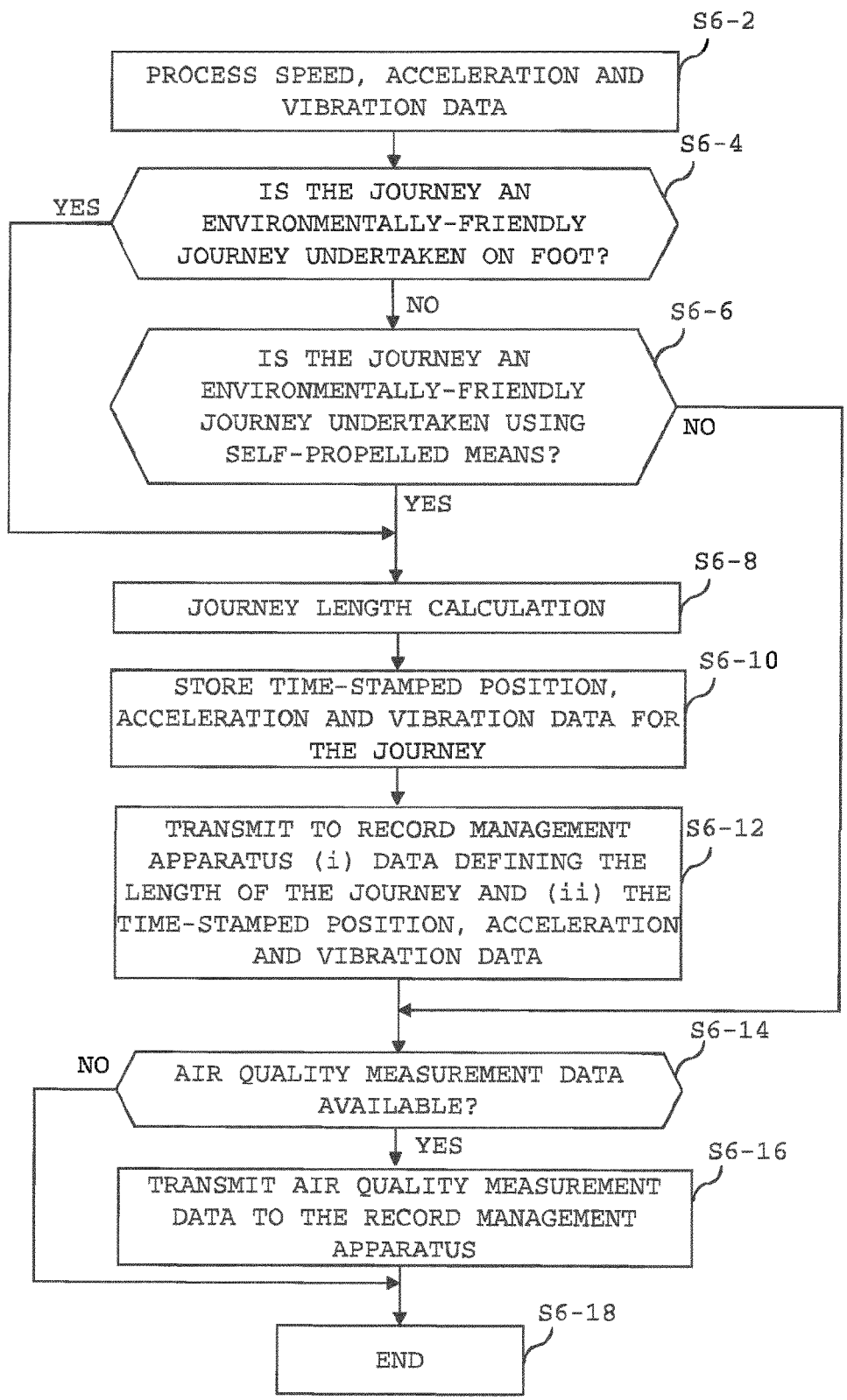
FIG. 6 shows the processing operations performed by a portable processing device carried by a person on a journey that comprises an environmentally-friendly journey undertaken on foot or using self-propelled means.

Referring now to FIG. 6, the processing operations will be described that are performed by portable processing device 80 in the event that it is determined at steps S5-2 and S5-4 that a journey has been started by the person carrying the portable processing device but that no signal has been detected from an identification device 120 in an environmentally-friendly vehicle.

At step S6-2, portable processing device 80 processes speed, acceleration and vibration data obtained from sensors in the portable processing device so as to determine, at steps S6-4 and S6-6, whether this data is indicative of an environmentally-friendly journey undertaken on foot or an environmentally-friendly journey undertaken using self-propelled means such as a bicycle, scooter, skateboard, roller-skates, rollerblades, etc.

If it is determined at step S6-4 that the person is undertaking an environmentally-friendly journey on foot, or if it is determined at S6-6 that the person is undertaking an environmentally-friendly journey using self-propelled means, then processing proceeds to step S6-8 to calculate the length of the journey. This journey length calculation may be updated for the duration that the speed, acceleration and/or vibration data indicate that the journey is continuing, so as to determine the total length the environmentally-friendly journey.

Optionally, at step S6-10, time-stamped position, acceleration and/or vibration data that has been processed at step S6-2 may be stored for different times and/or positions throughout the journey.

At step S6-12, portable processing device 80 transmits data to record management apparatus 110 defining the length of the environmentally-friendly journey undertaken on foot or undertaken using self-propelled means. Furthermore, if time-stamped position, acceleration and/or vibration data was stored at step S6-10 for the journey, then portable processing device 80 transmits this data as well to record management apparatus 110.

The transmission of data at step S6-12 may be performed as soon as the journey has finished, for example by transmitting the data using a cellular network. Alternatively, the transmission of data at step S6-12 may be delayed and transmitted, for example, using Wi-Fi when the portable processing device 80 is in range of a Wi-Fi router.

At step S6-14, a determination is made as to whether any air quality measurement data has been received from one or more air quality sensors 90 carried by the person.

If it is determined at step S6-14 that air quality measurement data has been received, then processing proceeds to step S6-16, at which the air quality measurement data is transmitted to record management apparatus 110. The transmission at step S6-16 may be performed at different times while a journey is continuing, as soon as the journey has ended, or at a delayed time thereafter. On the other hand if it is determined at step S6-14 that no air quality measurement data has been received, then the processing at step S6-16 is omitted.

Processing ends at step S6-18 and the portable processing device 80 enters a stand-by mode to await the start of the next journey.

Figure 7A:
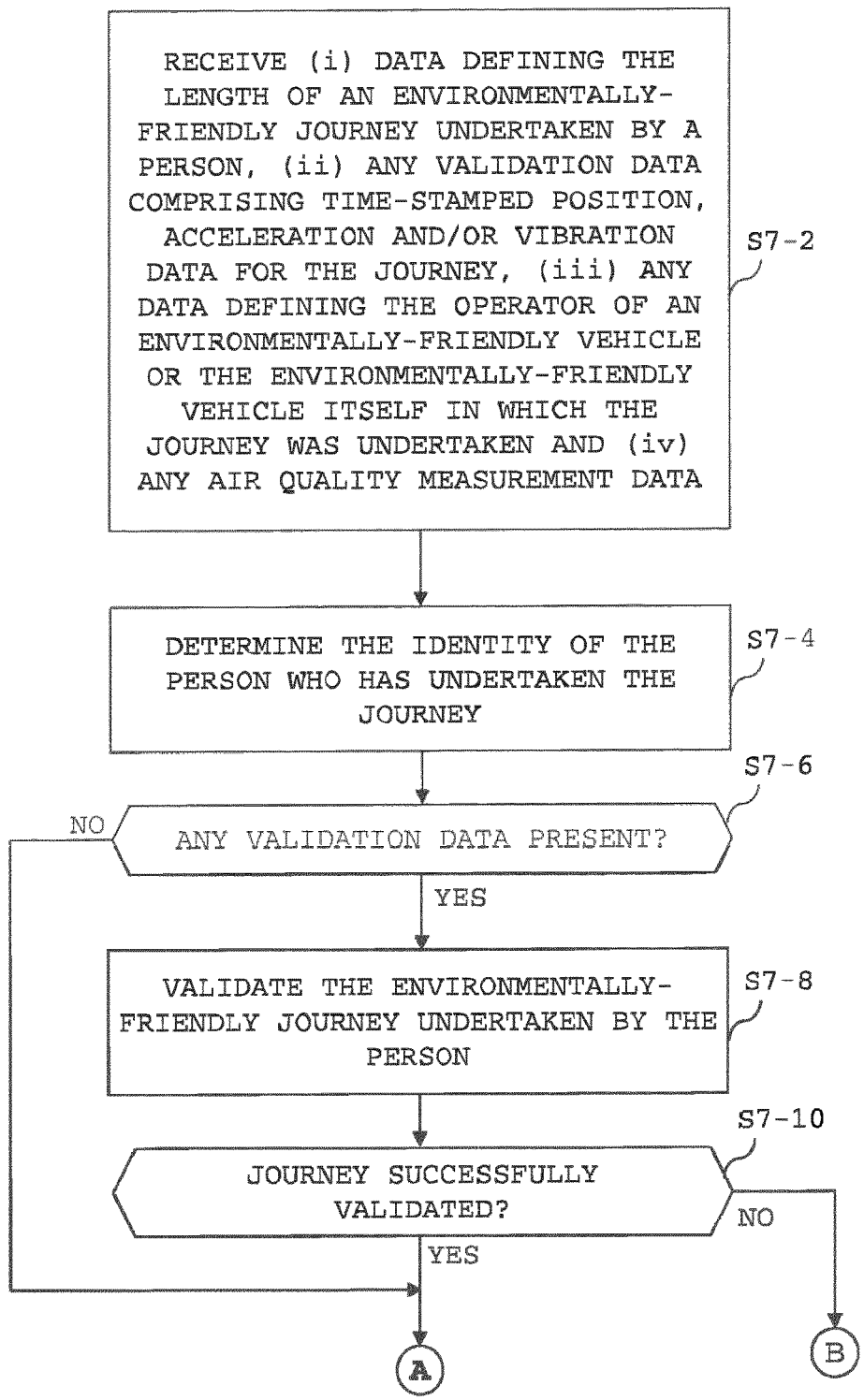
FIGS. 7a and 7b show processing operations performed by the record management apparatus.
Figure 7B:
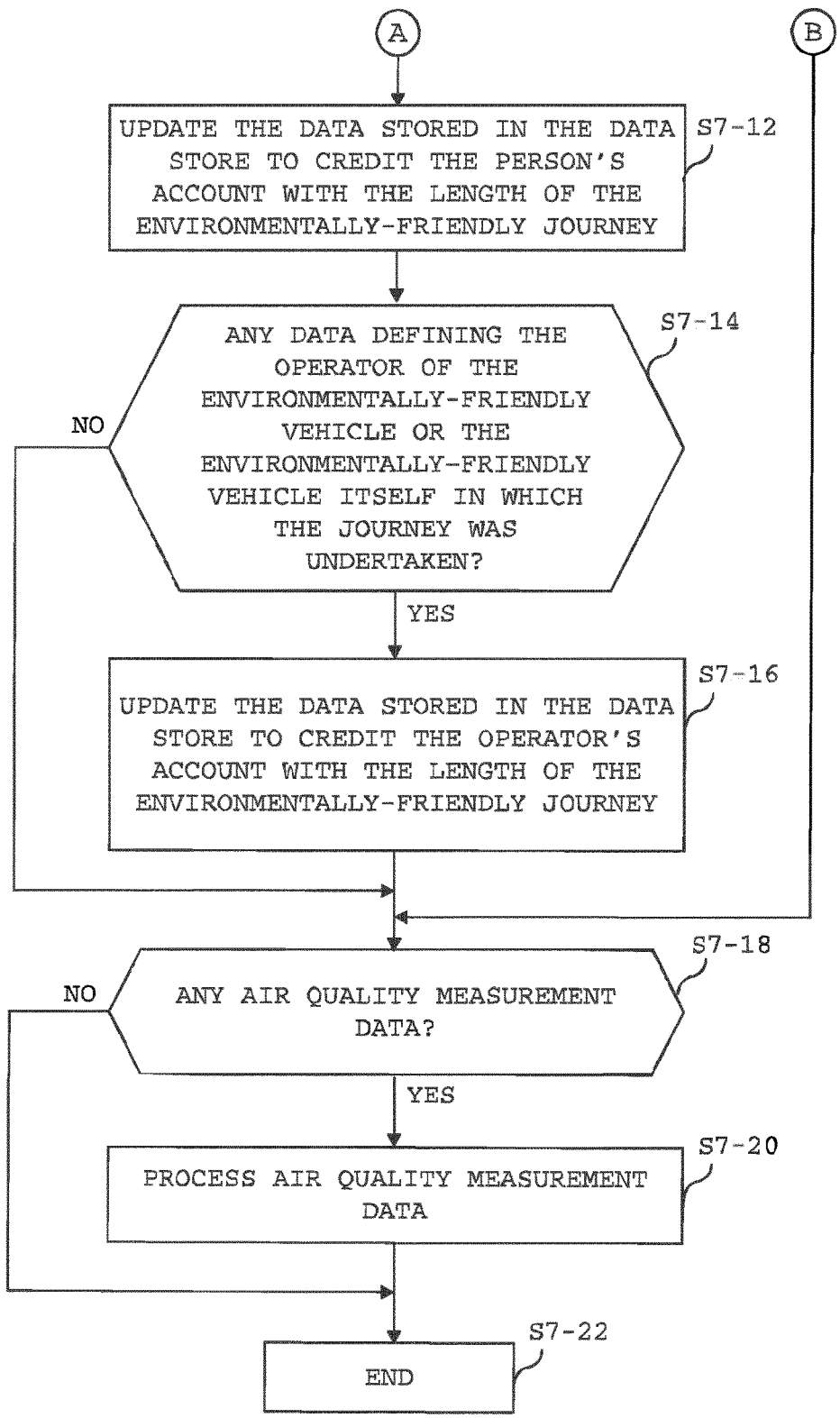
Figure 8:
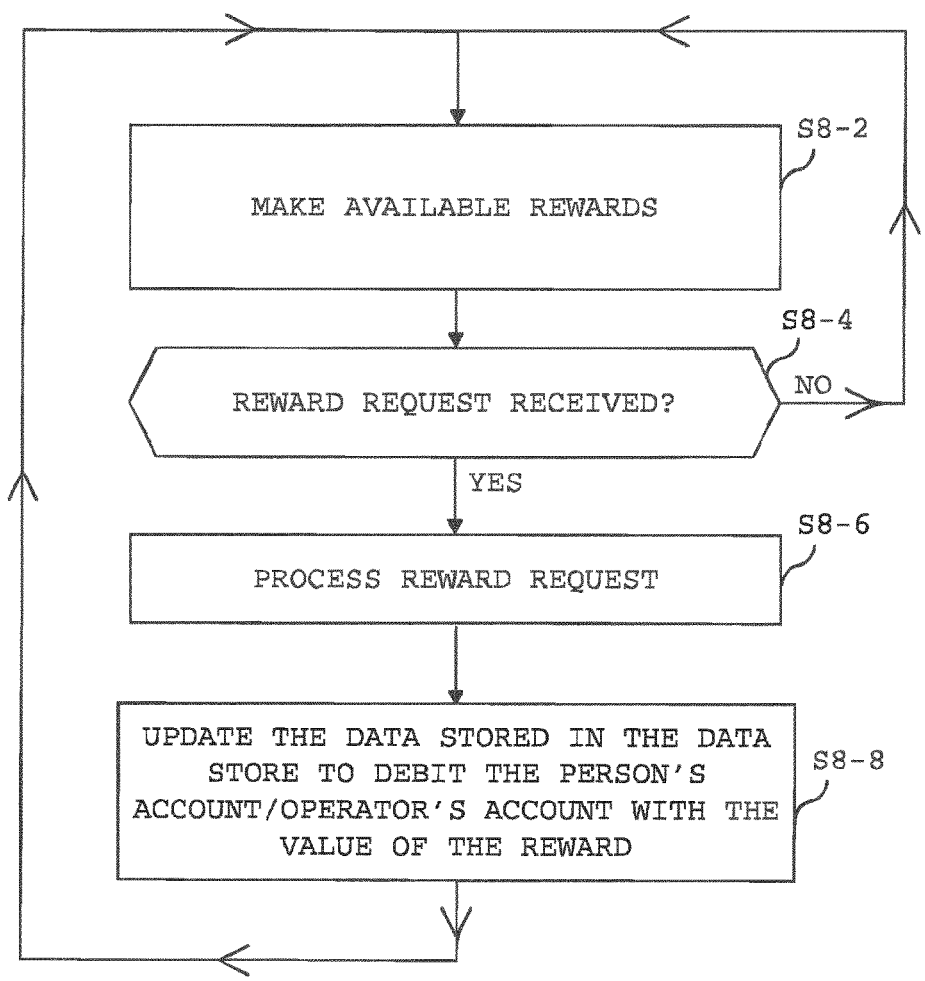
FIG. 8 shows further processing operations performed by the record management apparatus.

Turning now to FIGS. 7a, 7b and 8, the processing operations performed by record management apparatus 110 will be described.

At step S7-2, record management apparatus 110 receives data defining the length of an environmentally-friendly journey undertaken by a person. Optionally, record management apparatus 110 may also receive validation data comprising time-stamped position, acceleration and/or vibration data for the journey. As a further option, record management apparatus 110 may receive data defining the operator of the environmentally-friendly vehicle or the environmentally-friendly vehicle itself in which the journey was undertaken. As yet a further option, record management apparatus 110 may receive air quality measurement data recorded by one or more air quality sensors 90.

At step S7-4, the identity of the person who has undertaken the journey is determined. This may be done, for example, by determining the identity of the portable processing device 80 from which the data is received and then determining the identity of the person using a registration that has previously been stored in record management apparatus 110 which associates the portable processing device with a person. Alternatively, the identity of the person undertaking the journey may be transmitted to record management apparatus 110 as part of the journey data.

At step S7-6, a determination is made as to whether any validation data for the journey has been received.

If it is determined at step S7-6 that validation data has been received, then processing proceeds to step S7-8, at which the environmentally-friendly journey undertaken by the person is validated. By way of example, the validation at step S7-8 may be performed by comparing time-stamped position, acceleration and/or vibration data received from different portable processing devices 80 to determine if the different portable processing devices were carried by the same person (indicating that the journey is not valid because more than one person is trying to obtain credit for a journey that was undertaken by only a single person carrying the portable processing devices 80 of the different people).

At step S7-10, a determination is made as to whether the journey was successfully validated at step S7-8.

If it is determined at step S7-10 that the journey was not successfully validated, the processing proceeds to step S7-18, which will be described later. On the other hand, if it is determined at step S7-10 that the journey was successfully validated, or if it is determined at step S7-6 that no validation data is present, the processing proceeds to step S7-12.

At step S7-12, the data stored in data store 402 is updated to credit the account of the person identified at step S7-4 with the length of the environmentally-friendly journey. By way of example, the data stored in data store 402 may be updated so as to record (i) a value indicative of the total length of all environmentally-friendly journeys undertaken by the person and (ii) a value indicative of the journey length that the person has remaining to redeem against rewards (this value being for example, the total length of all environmentally-friendly journeys undertaken by the person less the values of rewards previously redeemed by the person).

At step S7-14, a determination is made as to whether any data was received at step S7-2 defining the operator of the environmentally-friendly vehicle or the environmentally-friendly vehicle itself in which the journey was undertaken.

If it is determined at step S7-14 that data has been received defining the operator or the environmentally-friendly vehicle, then processing proceeds to step S7-16, at which the data stored in data store 402 is updated to credit the operator's account with the length of the environmentally-friendly journey. This updating may be performed, for example, in the same way as the updating at step S7-12. On the other hand, if it is determined at step S7-14 that no data has been received defining the operator or the environmentally-friendly vehicle itself, then the processing at step S7-16 is omitted.

At step S7-18, a determination is made as to whether any air quality measurement data was received at step S7-2.

If it is determined at step S7-18 that air quality measurement data has been received, then processing proceeds to step S7-20, at which the air quality measurement data is processed. This processing may, for example, integrate the air quality measurement data recorded by a portable processing device 80 for different locations with the air quality measurement data recorded by different portable processing devices 80 and other available air quality data for the same locations so as to make available integrated air quality data for download. On the other hand, if it is determined at step S7-18 that no air quality measurement data has been received, then the processing at step S7-20 is omitted.

Processing ends at step S7-22, and record management apparatus 110 awaits the next receipt of data.

FIG. 8 shows the processing operations performed by record management apparatus 110 with regard to rewards.

At step S8-2, rewards are made available to people and, optionally, operators of environmentally-friendly vehicles that have registered to have accounts with record management apparatus 110.

The rewards and the way in which they are made available may vary considerably and may take many different forms. By way of example, a monetary value may be assigned to miles (or kilometers or other distances) accumulated by a person and/or operator in their account. For example, a monetary value 500 miles=$2.50 may be assigned or any other appropriate value. The individual or operator may then be permitted to obtain goods or services to the value assigned in exchange for redeeming their miles. These goods or services may themselves be environmentally-friendly goods and services. An example service may be travel on one of the environmentally-friendly vehicles, so that a person can redeem miles in exchange for the payment of their transport fare on an environmentally-friendly bus 40 or an environmentally-friendly train 60. Record management apparatus 110 may be configured to enable a person and/or operator to donate their rewards to registered charities. An exchange for miles as a virtual currency may be established and the exchange of miles for hard currency could be provided. In addition or instead, miles could be treated as carbon trading units and traded on carbon exchanges. By way of further example, an operator could offset its carbon emissions from non-environmentally-friendly vehicles by exchanging miles under certified emissions trading schemes.

At step S8-4, a determination is made as to whether a request for a reward has been received.

When it is determined at step S8-4 that a request for a reward has been received, then processing proceeds to step S8-6 to process the reward request. The processing at step S8-6 varies in dependence upon the nature of the reward but may include, for example, providing the reward in accordance with the request.

At step S8-8, the data stored in the data store 402 for the person/operator making the request for the reward is updated to debit the account of the person/operator with the value of the reward.

A simple example will now be provided to illustrate how rewards may be made available and how revenue may be generated by the record management apparatus. An individual, Jane Smith, registers with the record management apparatus, downloads the app to her smartphone, and purchases a bracelet with air quality sensors from a website provided by the recorded management apparatus. Jane then goes about her normal life as a graphic designer working in San Francisco. Under the app privacy controls, Jane selects to provide anonymised air quality data to the record management apparatus as she travels and selects to receive promotions and offers from validated merchants. She tends to either cycle to work (if it is a nice day) or take an environmentally-friendly bus if it is not. Her daily commute is 6 miles each way (by cycle) and 5 miles by bus with a half mile walk to/from the bus stop at each end. When Jane has accrued 500 miles in her account, she receives a message on her smartphone via the app congratulating her on achieving this 500 mile milestone and informing her that on her route to work there is a coffee shop offering a free fairtrade™ coffee in exchange for her popping in and redeeming her first 500 miles at this store. She can see the location of the store on her smartphone (via the app) and next time she cycles to work she calls in to obtain her free coffee (normally priced at $2.50) and redeems 500 miles to obtain the coffee without paying any money. The shop's point of sale device connects with the record management apparatus which credits the 500 miles that Jane redeemed to the shop's account and debits 500 miles from Jane's account. The data management apparatus charges the store a predetermined percentage (for example 1%) of the value of the coffee. While Jane is at the store she notices that it is selling fairtrade™ certified coffee beans (priced at $3.99 per packet) and she buys two packets, one for home and one for the office (at a total cost of $7.98). This generates a further payment by the store to the owner of the data management apparatus of a predetermined percentage of the sale (for example 1%). Jane decides to donate the next 500 miles she generates to support a national asthma charity as she is aware that the owner of the record management apparatus matches all donations to their charities. Jane notes that the accrual of miles by her and other residents in her borough contributes to the creation of a fund to invest in projects that improve air quality and the environment within her local area. Jane uses the social network aspects of the app to communicate and share information with fellow members of the network, for example to encourage the installation of an electric vehicle charging point, or a new electric bus route, based upon an aggregation of journey and air quality information provided by members of the network.

It will, of course, be appreciated that rewards may be made available in many other different forms than those described herein.

[Embodiment 2]

Figure 9:
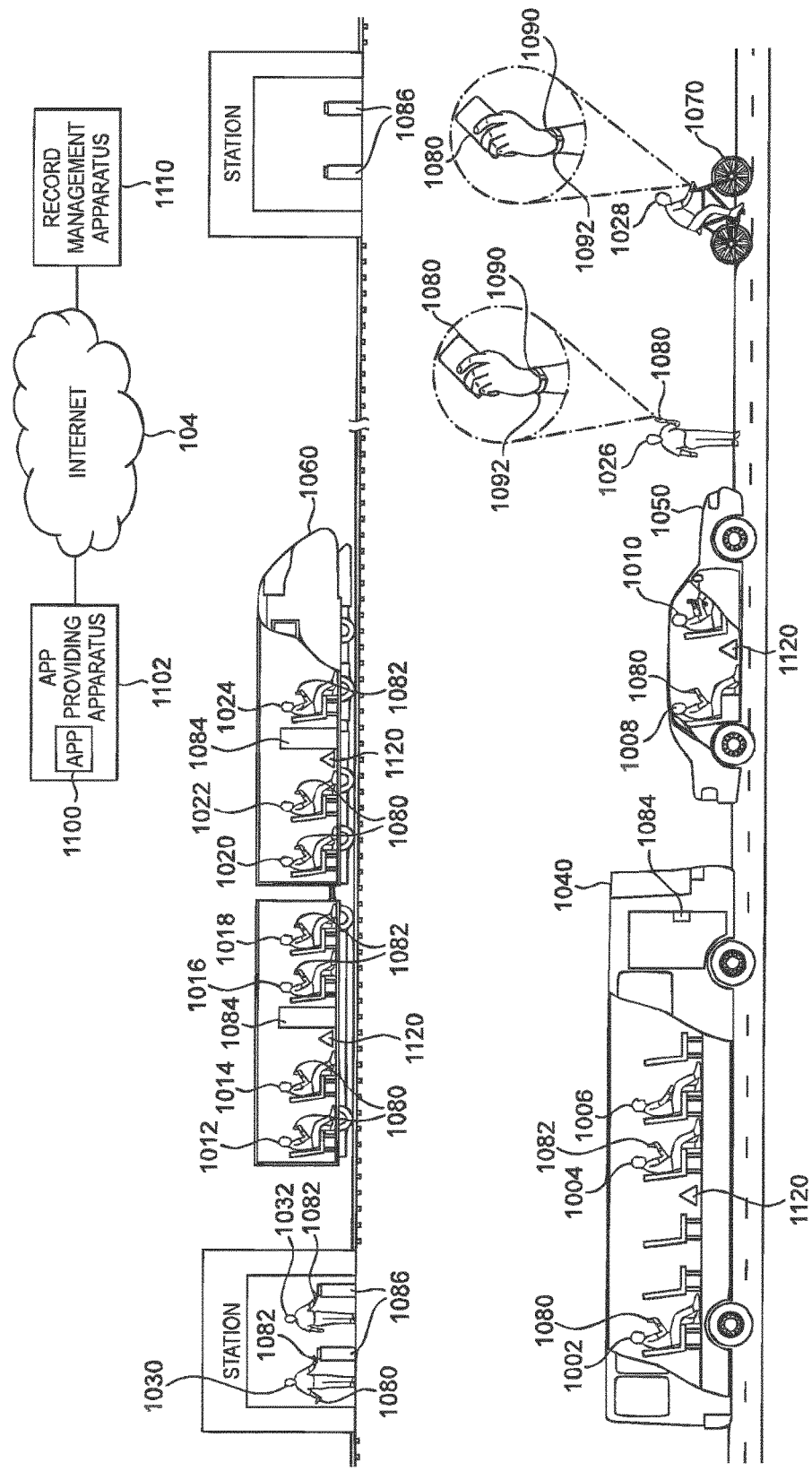
FIG. 9 semantically illustrates technology that is employed in a second embodiment when a plurality of people undertake journeys using different modes of environmentally-friendly transport.

FIG. 9 semantically illustrates the technical components of a second embodiment that are used by a plurality of people undertaking different journeys using different modes of transport. More particularly, in the example of FIG. 9, the people 1002, 1004 and 1006 make respective journeys on a bus 1040, the people 1008, 1010 undertake a journey in a car 1050, the people 1012-1024, 1030 and 1032 make respective journeys on a train 1060, the person 1026 undertakes a journey on foot, and the person 1028 undertakes on self-propelled means comprising a bicycle.

As in the first embodiment, it will be appreciated that the technology of the second embodiment can be applied to environmentally-friendly modes of transport other than those shown in FIG. 9. For example, the technology can be applied to vehicles such as taxis, trams, monorail trains, underground trains, motorcycles, mopeds, boats, etc. Similarly, the technology can be applied to other self-propelled means such as scooters, skateboards, roller-skates, roller-blades, etc.

In this embodiment, each person undertaking a journey carries a portable processing device 1080 and/or a card 1082 carrying data that identifies the person. The portable processing device 1080 may comprise a mobile telephone, smart watch, tablet computer, e-book reader or any other form of portable computer processing apparatus. Each portable processing device 1080 may comprise multiple separate parts configured to communicate with each other or comprise one self-contained unit. The card 1082 may comprise a travel card, credit card, debit card, or any other form of card carrying data identifying the user. The data may be stored, for example, in a magnetic strip, chip or other form of storage medium on the card 1082.

As in the first embodiment, a person undertaking a journey may optionally carry one or more air quality sensors 1090 for measuring one or more air quality parameters. Such air quality sensors 1090 are semantically in FIG. 9 for people 1026 and 1028 who carry the air quality sensors 1090 on bracelets 1092 (although they could be carried in different ways instead).

Each portable processing device 1080 has stored therein an app 1100 downloaded from an app providing apparatus 1102 for example via the internet 104 or provided pre-installed by the manufacturer of the portable processing device 1080. The app 1100 comprises computer program instructions which, when executed, cause the portable processing device 1080 to perform processing operations as described below.

Each environmentally-friendly vehicle in which a person may undertake a journey is provided with at least one of a processing device 1120 operable to work with portable processing devices 1080 carried by people on the environmentally-friendly vehicle and a processing device 1084 operable to work with cards 1082 carried by people on the environmentally-friendly vehicle.

The processing devices 1120, 1084 are fitted only to vehicles that are categorised as environmentally-friendly vehicles. A vehicle may be categorised as an environmentally-friendly vehicle in a number of different ways. For example, a vehicle may be categorised as an environmentally-friendly vehicle if its emissions are below environmental emission standards set, for example, by an authoritative organisation. In addition or instead, all or a predetermined amount of a vehicle's energy may need to derived from renewable energy sources in order for the vehicle to be categorised as an environmentally-friendly vehicle. An authoritative organisation may be tasked with validating and certifying that vehicles meet the necessary environmentally-friendly standards and authorising the fitting of a processing device 1120 and/or 1084.

Each processing device 1120, 1084 may be fitted to the environmentally-friendly vehicle during original manufacture or retro-fitted. Each processing device 1120, 1084 can be powered by connecting it to the power supply of the environmentally-friendly vehicle in which it is fitted. In addition or instead, each processing device 1120, 1084 can be powered with conventional non-rechargeable batteries, which are replaced when the batteries are empty. Alternatively, each processing device 1120, 1084 can be powered using energy harvesting/scavenging techniques, for example by harvesting ambient background radio-frequency (RF) energy using techniques such as those disclosed in co-pending patent applications GB 1314307.8 and PCT/GB2014/052431, the full contents of which are incorporated herein by cross-reference, or by gathering kinetic, thermal, solar, wind, and/or chemical gradient energy. As a further alternative, one or more rechargeable batteries could be provided for each processing device 1120, 1084 and the battery or batteries could be recharged using inductive power transfer, for example using techniques disclosed in copending patent applications GB 1215152.8, GB 1309691.2, GB 1321267.5, PCT/GB2013/051456, PCT/GB/ 2014/051656, CA 2817288 and MX/A/2013/006253, the full contents of which are incorporated herein by cross-reference, or by using acoustic waves (ultrasound) or optical power, such as lasers.

Each processing device 1120 is operable to receive identifying data from a portable processing device 1080 carried by a person in the environmentally-friendly vehicle. This identifying data is transmitted by each portable processing device 1080 using a short-range communication technique such as Bluetooth. Each processing device 1120 is further operable to determine, for each person for which identifying data is received, a length of the journey undertaken by the person in the environmentally-friendly vehicle. Furthermore, each processing device 1120 is operable to transmit data to record management apparatus 1110 defining, for each person for which identifying data was received, the identifying data and the determined length of the journey undertaken by the person in the environmentally-friendly vehicle.

Each processing device 1084 is operable to read identifying data from a card 1082 carried by a person in the environmentally-friendly vehicle. By way of example, each processing device 1084 is positioned near a door of the environmentally-friendly vehicle so that the person can place his/her card on, or near to, the processing device 1084 upon entering and also upon leaving the environmentally-friendly vehicle so that data from the card 1082 can be read by the processing device 1084 using a contact or contactless data reading technique. Each processing device 1084 is further operable to determine, for each person for which identifying data was received from a card 1082, the length of the journey undertaken by the person in the environmentally-friendly vehicle. Furthermore, each processing device 1084 is operable to transmit data to record management apparatus 1110 comprising the identifying data for each person and data defining the determined length of the journey undertaken by the person in the environmentally-friendly vehicle.

In addition to, or instead of, processing devices 1084, card readers 1086 may be provided at fixed locations on a route of environmentally-friendly vehicles. For example, card readers 1086 may be provided at the stations at which environmentally-friendly trains stop and may be positioned at bus stops at which environmentally-friendly buses stop. The card readers 1086 at stations may be connected together via a network and may be configured to determine the length of a journey undertaken by a person on an environmentally-friendly train by determining the station at which the person entered and the station at which the person exited (this determination being made by reading identifying data from the card 1082 carried by the person using a contact or contactless data reading technique). The determined length of the journey is then transmitted to record management apparatus 1110 along with the identifying data of the person. Card readers 1086 at bus stops may be similarly connected together and arranged to determine journey lengths and report the journey lengths to record management apparatus 1110.

Record management apparatus 1110 stores data defining, for each person, the length of environmentally-friendly journeys undertaken by that person, and furthermore makes available rewards dependent upon the length of environmentally-friendly journeys undertaken.

The technical components illustrated in FIG. 9 and the processing operations formed thereby will now be described in more detail.

Figure 10:
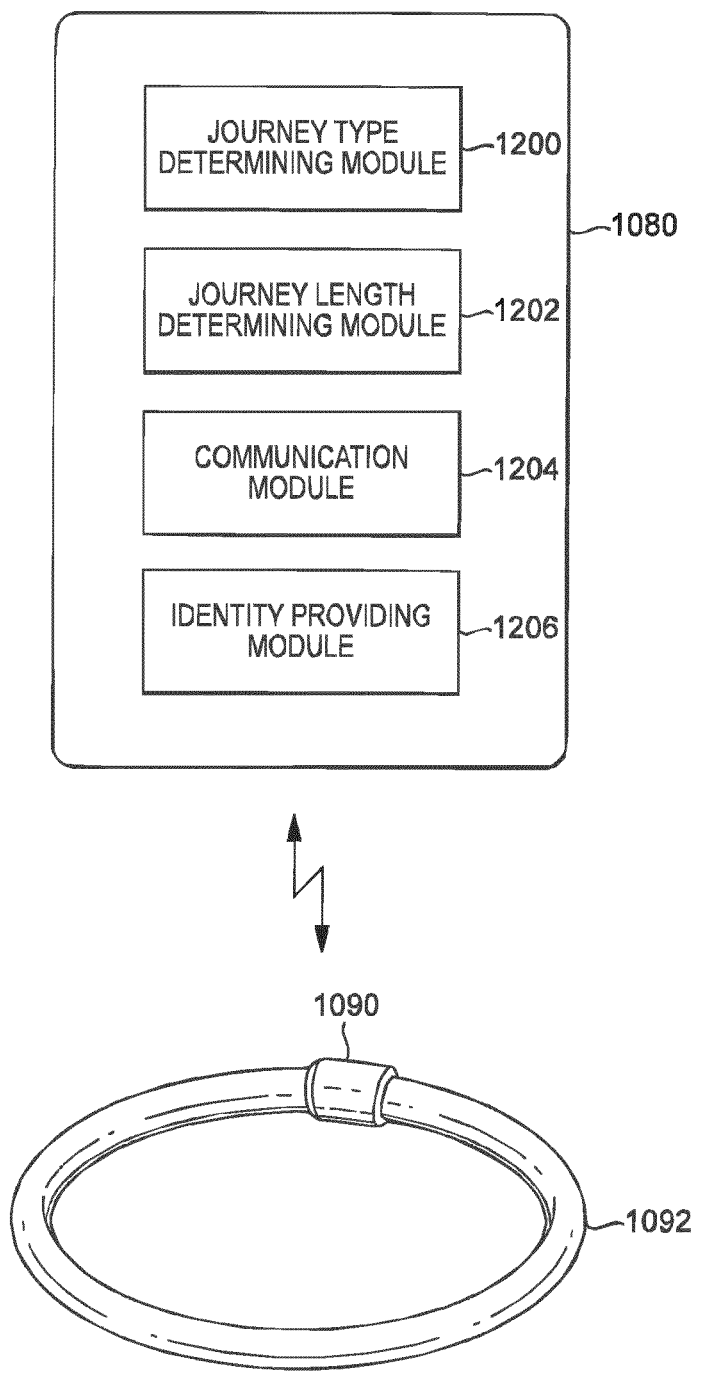
FIG. 10 semantically illustrates the functional processing modules of a portable processing device in the second embodiment carried by a person undertaking his/her journey, as well as the optional air quality sensor(s) that may also be carried by the person.

FIG. 10 semantically illustrates the portable processing device 1080 carried by a person undertaking a journey and the optional air quality sensor(s) 1090.

Referring to FIG. 10, when the processor(s) of the portable processing device 1080 executes the computer program instructions of the app 1100, the portable processing device 1080 becomes configured to provide a number of different notional functional processing units, which, in this embodiment, comprise journey type determining module 1200, journey length determining module 1202, communication module 1204 and identity providing module 1206.

Journey type determining module 1200 is operable to determine whether a journey undertaken by a person carrying the portable processing device 1080 is an environmentally-friendly journey comprising a journey undertaken on foot or a journey undertaken on self-propelled means such as a bicycle, scooter, skateboard, roller-skates, rollerblades, etc.

The journey type determining module 1200 may be operable to determine if a journey is undertaken on foot or on self-propelled means in dependence upon at least one of speed during the journey, acceleration during the journey and vibrations during the journey.

Journey length determining module 1202 is operable to determine a length of an environmentally-friendly journey undertaken by the person carrying the portable processing device 1080. For example, journey length determining module 1202 may be configured to determine the positions of points (such as positions determined by GPS or other means) throughout the journey and to determine the distance between the points, thereby determining the total length of the journey.

Communication module 1204 is operable to transmit journey data to record management apparatus 1110 defining the length of each environmentally-friendly journey undertaken by the person carrying the portable processing device 1080. Each portable processing device 1080 may identify itself to record management apparatus 1110 during the communication so that record management apparatus 1110 can identify the owner of the portable processing device 1080 using a previous registration made by the person which provides record management apparatus 1110 with the person's details in association with the ID of the portable processing apparatus 1080. Alternatively, communication module 1204 may be configured to transmit to record management apparatus 1110 data defining a personal ID entered by the person carrying the portable processing device for example using an input keypad, touch-sensitive screen or other input device.

Optionally, if portable processing device 1080 is to be used with a processing device 1120 in an environmentally-friendly vehicle, the portable processing device 1080 further comprises an identity providing module 1206. Identity providing module 1206 is operable to provide an identity of at least one of the portable processing device and the person carrying the portable processing device to the processing device 1120 in the environmentally-friendly vehicle in which the person is travelling. Identity providing module 1206 may provide the identity by transmitting identifying data using a short-range communication technique, such as Bluetooth.

As a further option, the communication module 1204 may be operable to transmit validation data to the record management apparatus 1110 for an environmentally-friendly journey, the validation data comprising at least one of position data, acceleration data and vibration data.

As yet a further option, portable processing device 1080 may be operable to receive signals, for example by Bluetooth or other short-range communication technique, from one or more air quality sensors 1090 carried by the person. In such a case, communication module 1204 is further operable to transmit air quality measurement data received from the air quality sensor(s) to the record management apparatus 1110.

All transmissions by communication module 1204 to record management apparatus 1110 may be made in any appropriate way, for example using a cellular network or using Wi-Fi when the portable processing device 1080 is within range of a Wi-Fi router.

Portable processing device 1080 is optionally further operable to receive air quality data from record management apparatus 1110 and to provide the air quality data to the person carrying the portable processing device, for example by displaying the data on a display.

Figure 11:
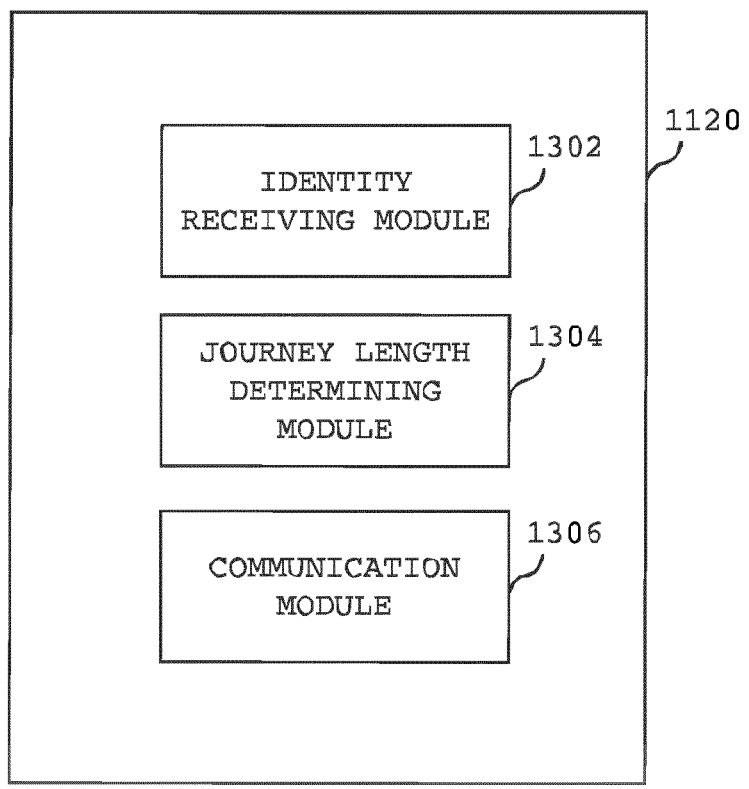
FIG. 11 shows the functional processing modules of a first processing device that may be provided in an environmentally-friendly vehicle in the second embodiment.

FIG. 11 shows the functional processing modules of processing device 1120 provided in an environmentally-friendly vehicle.

Referring to FIG. 11, processing device 1120 comprises an identity receiving module 1302, a journey length determining module 1304 and a communication module 1306.

Identity receiving module 1302 is operable to receive identifying data from a portable processing device 1080 of a person in the environmentally-friendly vehicle.

Journey length determining module 1304 is operable to determine, for each person for which identifying data is received, a length of the journey undertaken by the person in the environmentally-friendly vehicle. For example, journey length determining module 1304 may be configured to determine the positions of points (such as positions determined by GPS or other means) throughout the journey and to determine the distance between the points, thereby determining the total length of the journey. The positions of points may be obtained in a number of different ways, for example by providing a GPS positioning unit in processing device 1120 or by interfacing the processing device 1120 to a GPS satellite navigation system in the environmentally-friendly vehicle. Alternatively, journey length determining module 1304 may interface with the milometer of the environmentally-friendly vehicle to determine the length of a journey undertaken by a person.

Communication module 1306 is operable to transmit data to record management apparatus 1110 defining, for each person for which identifying data is received, the identifying data and the determined length of the journey undertaken by the person in the environmentally-friendly vehicle. Optionally, the communication module 1306 is further operable to transmit data to record management apparatus 1110 identifying at least one of the operators of the environmentally-friendly vehicle and the environmentally-friendly vehicle itself. The operator may be, for example, the organisation which owns a fleet of vehicles to which the environmentally-friendly vehicle belong (such as the bus company which operates bus 1040 or the train company which operates train 1060 in the example of FIG. 9).

Figure 12:
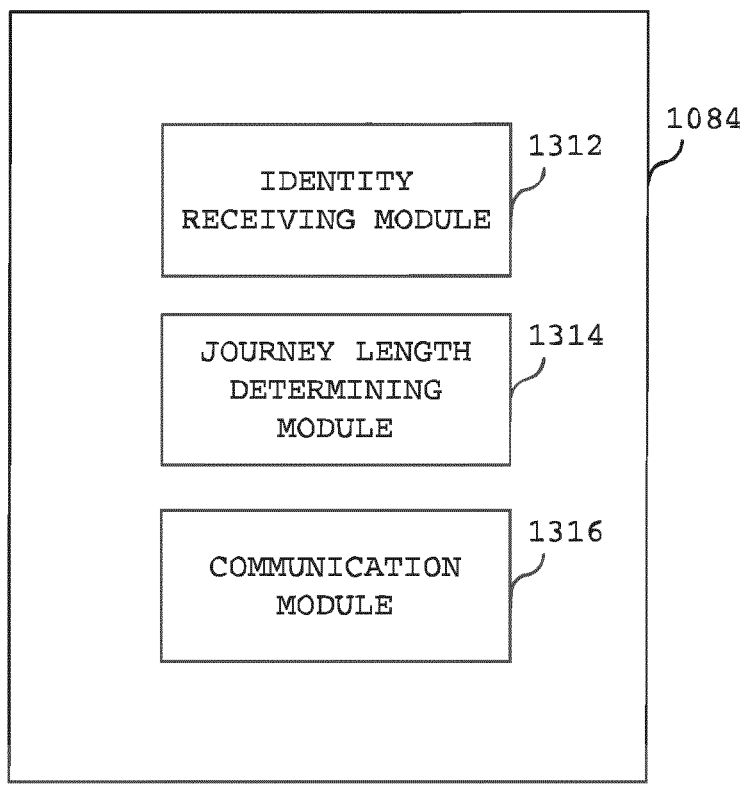
FIG. 12 shows the functional processing modules of a second processing device that may be provided in an environmentally-friendly vehicle in the second embodiment.

FIG. 12 shows the functional processing modules of processing device 1084 in an environmentally-friendly vehicle.

Referring to FIG. 12, processing device 1084 comprises an identity receiving module 1312, a journey length determining module 1314 and a communication module 1316.

Identity receiving module 1312 is operable to read identifying data from a card 1082 carried by a person.

Journey length determining module 1314 is operable to determine, for each person for which identifying data is received, a length of the journey undertaken by the person in the environmentally-friendly vehicle. For example, journey length determining module 1314 may be configured to determine positions of points (such as positions determined by GPS or other means) throughout the journey and to determine the distance between the points, thereby determining the total length of the journey. The positions of points may be obtained in a number of different ways, for example by providing a GPS positioning unit in processing device 1084 or by interfacing the processing device 1084 to a GPS satellite navigation system in the environmentally-friendly vehicle. Alternatively, journey length determining module 1314 may interface with the milometer of the environmentally-friendly vehicle to determine the length of a journey undertaken by a person.

Communication module 1316 is operable to transmit data to record management apparatus 1110 defining, for each person for which identifying data was received, the identifying data and the determined length of the journey undertaken by the person in the environmentally-friendly vehicle. Optionally, communication module 1316 is further operable to transmit data to record management apparatus 1110 identifying at least one of the operators of the environmentally-friendly vehicle and the environmentally-friendly vehicle itself.

Figure 13:
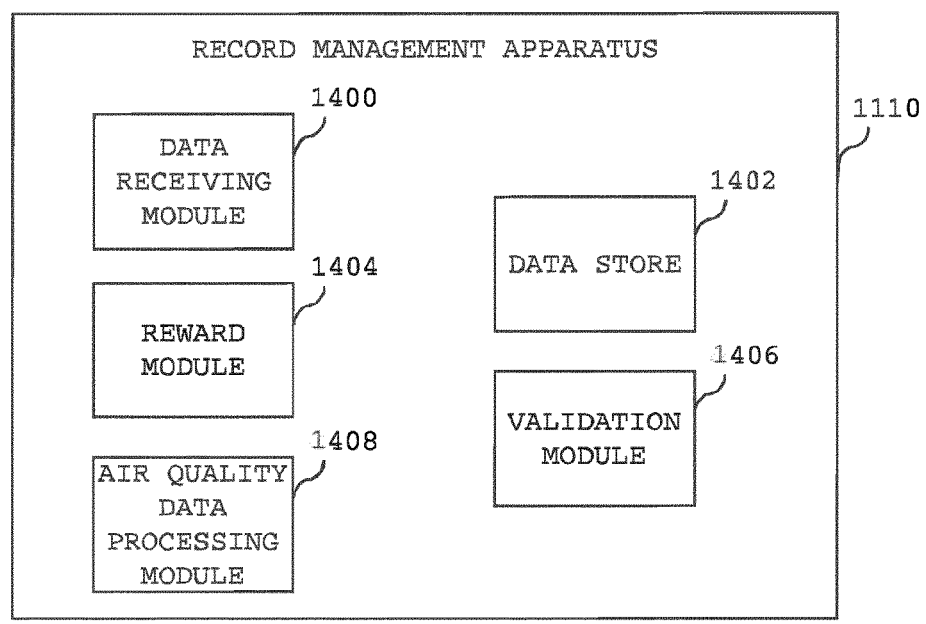
FIG. 13 shows the functional processing modules of record management apparatus in the second embodiment.

FIG. 13 shows the functional processing modules of record management apparatus 1110. Record management apparatus 1110 may comprise multiple separate parts configured to communicate with each other or a single apparatus. Record management apparatus 1110 may be a cloud-based server apparatus, for example.

Referring to FIG. 13, the functional processing modules 1400-1408 of record management apparatus 1110 are the same as the functional processing modules 400-408 of record management apparatus 110 in the first embodiment, with the exception of data receiving module 1400 which is operable to receive data not only from portable processing devices 1080, but also from processing devices 1020 and 1084, as well as networks of card readers 1086. As the processing modules of record management apparatus 1110 have been described previously, they will not be described again here.

Having described the functional components of the different apparatus shown in FIG. 9, the processing operations performed by those components will now be described.

The processing operations performed by a portable processing device 1080 that is carried by a person undertaking a journey on foot or using self-propelled means are the same as the processing operations shown in, and described with reference to, FIG. 6 in the first embodiment. Accordingly, these processing operations will not be described again here.

Figure 14:
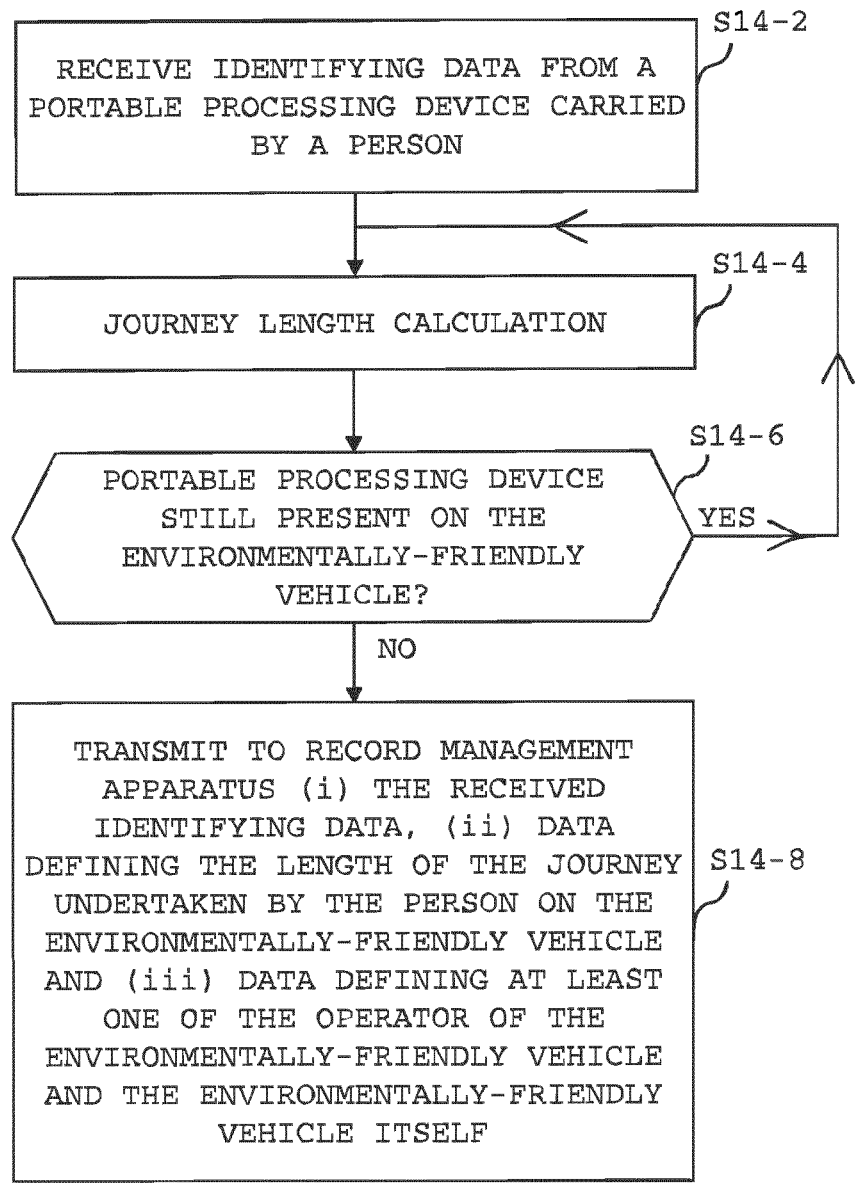
FIG. 14 shows the processing operations performed by a first processing device in an environmentally-friendly vehicle in the second embodiment.

FIG. 14 shows the processing operations performed by processing device 1120 in an environmentally-friendly vehicle.

At step S14-2, identifying data is received from a portable processing device 1080 carried by a person in the environmentally-friendly vehicle.

At steps S14-4 and S14-6, processing is performed to calculate the length of the journey undertaken by the person in the environmentally-friendly vehicle. More particularly, the journey length calculation is performed and updated at step S14-4 for all of the time that it is determined at step S14-6 that the portable processing device 1080 is still present in the environmentally-friendly vehicle. It may be determined that the portable processing device 1080 is present in the environmentally-friendly vehicle, for example by the portable processing device 1080 constantly, or intermittently, transmitting its identifying data using a short-range communication technique, such as Bluetooth. In this way the identifying data will be received by processing device 1120 when the user enters the environmentally-friendly vehicle and remains therein, but the identifying data will no longer be received when the portable processing device 1080 leaves the vehicle because it becomes quickly out-of-range for detection by the processing device 1120.

At step S14-8, data is transmitted to record management apparatus 1110 comprising the identifying data received at S14-2 and data defining the length of the journey undertaken in the environmentally-friendly vehicle. Optionally, data may also be transmitted defining at least one of the operator of the environmentally-friendly vehicle and the environmentally-friendly vehicle itself.

Figure 15:
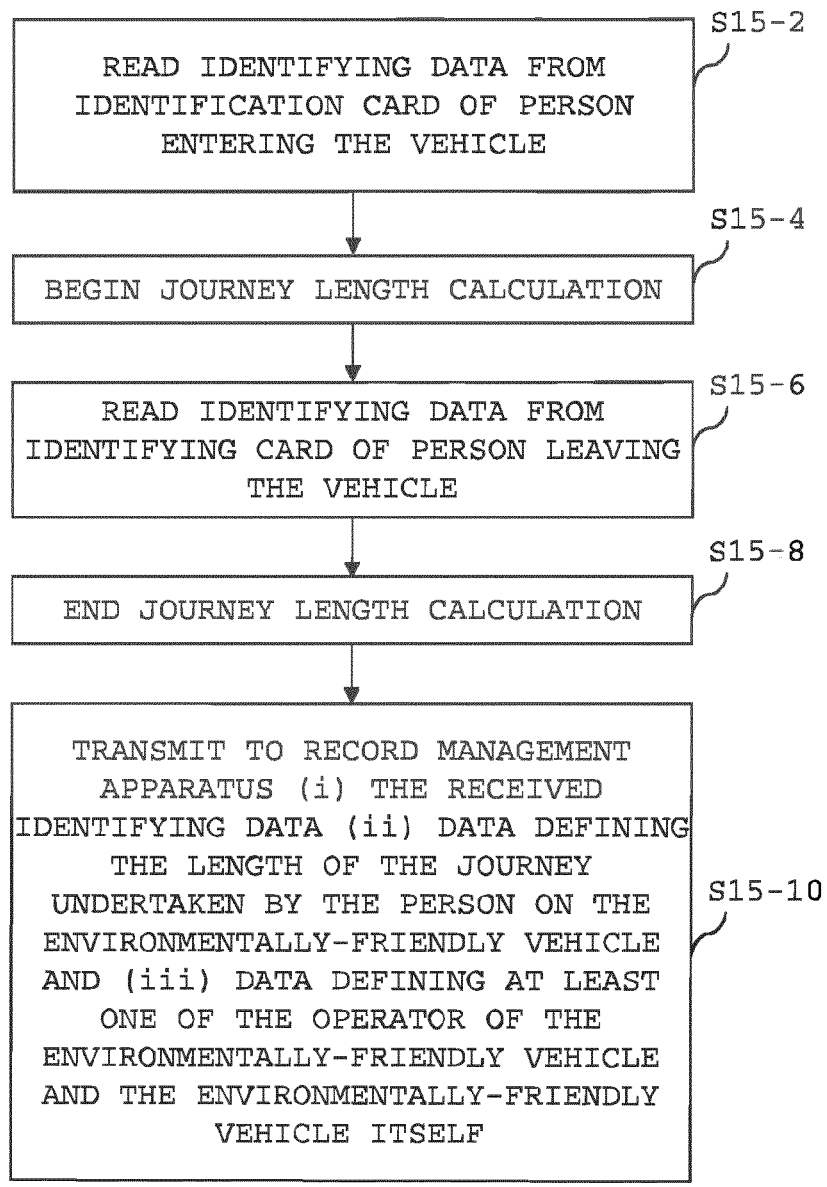
FIG. 15 shows the processing operations performed by a second processing device in an environmentally-friendly vehicle in the second embodiment.

FIG. 15 shows the processing operations performed by a processing device 1084 in an environmentally-friendly vehicle.

At step S15-2, data is read form a card of a person entering the vehicle. The data may be read using a contact and/or contactless data reading technique.

At step S15-4 calculation of the journey length begins.

At step S15-6, identifying data is read from the card of the person leaving the vehicle. The data may be read using a contact and/or contactless data reading technique.

At step S15-8 the journey length calculation ends.

At step S15-10, data is transmitted to record management apparatus 1110 comprising the identifying data received at step S15-2 and data defining the length of the journey undertaken by the person in the environmentally-friendly vehicle. Optionally, data is also transmitted defining at least one of the operator of the environmentally-friendly vehicle and the environmentally-friendly vehicle itself.

The processing operations performed by record management apparatus 1110 are the same as those shown in, and described with reference to, FIGS. 7a, 7b and 8 in the first embodiment, with it being noted that the data received at step S7-2 may be received from a portable processing device 1080, a processing device 1120, a processing device 1084 and/or a network of card readers 1086. As the processing operations of the record management apparatus have been described previously, they will not be described again here.

Having described exemplary embodiments of the present invention, it will be understood that innovative technology has been disclosed which motivates and rewards people for choosing environmentally-friendly transport and which may also be employed to motivate and reward providers of environmentally-friendly transport. The degree of environmentally-friendliness required for a vehicle to qualify can be set and changed as required and as environmentally-friendly transport technology and energy generation techniques develop. Ultimately, a vehicle could be required to travel without causing any pollution using energy produced from a completely renewable energy source so that each mile travelled is a "clean mile".

The technology described herein could enable governments to participate in and support a global connected social and physical infrastructure network that would enable a global community of people to acquire environmentally-friendly miles in any country, city or state, so encouraging an environmentally-sustainable travel and tourism business, which is a major contribution of GDP growth to certain cities and states. For example, a city/state could promote its transport infrastructure as being environmentally-friendly and part of the reward programme so that visitors could add miles to their accounts during a visit. Also the generation of "clean miles" within a certain local area of a city could be used to judge the demand and support from residents for improvements to local infrastructure projects that would improve air quality, such as sensor networks, electric vehicle charging infrastructure, cycle routes, new public transport routes etc. The generation of "clean miles" could itself be used as a funding mechanism for such projects.

Figure 16:
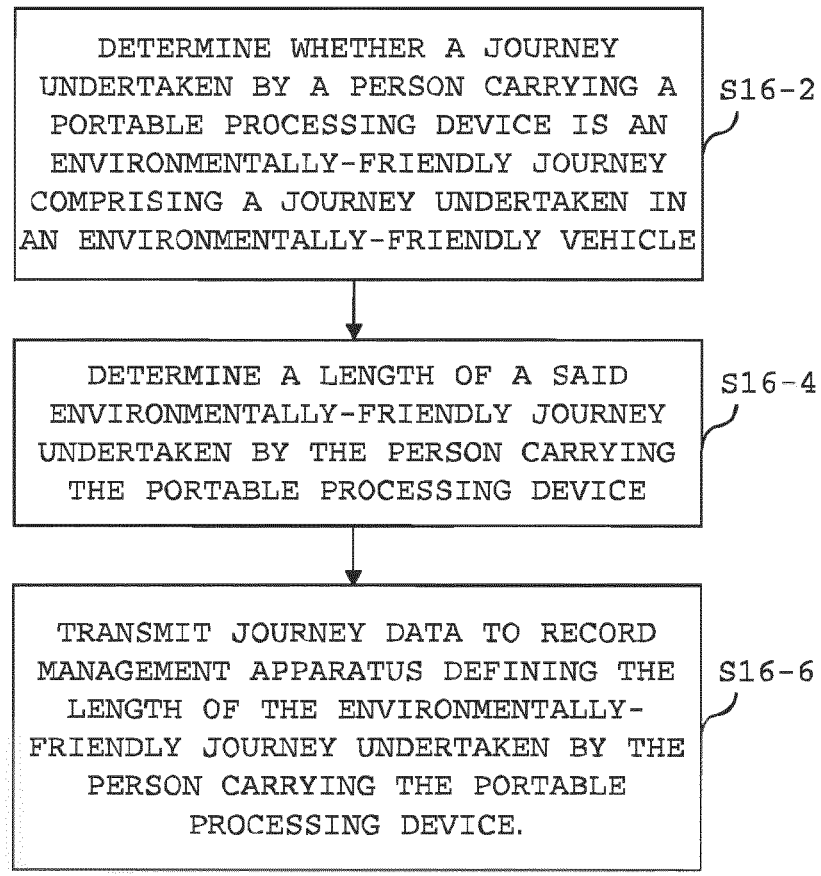
FIG. 16 shows processing operations performed by a portable processing device in embodiments.

It will be further understood that a portable processing device has been disclosed which performs processing operations as shown in FIG. 16.

Referring to FIG. 16, at step S16-2 the portable processing device determines whether a journey undertaken by a person carrying a portable processing device is an environmentally-friendly journey comprising a journey undertaken in an environmentally-friendly vehicle.

At step S16-4, the portable processing device determines a length of a said environmentally-friendly journey undertaken by the person carrying the portable processing device.

At step S16-6, the portable processing device transmits journey data to record management apparatus defining the length of an environmentally-friendly journey undertaken by the person carrying the portable processing device.

Figure 17:
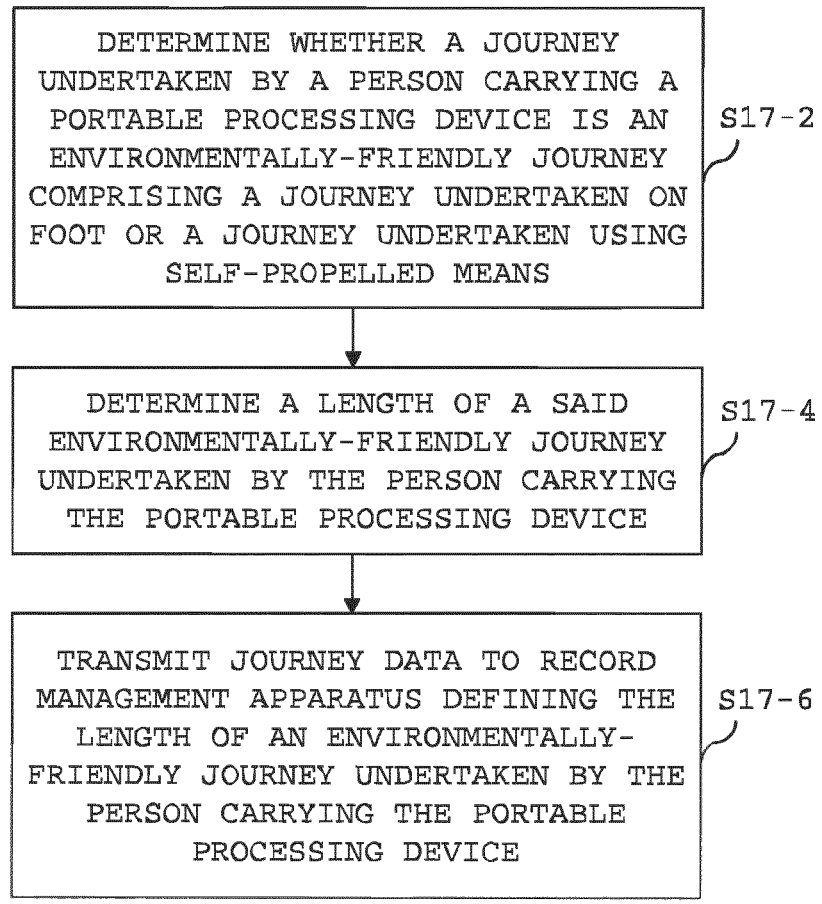
FIG. 17 shows processing operations performed by a portable processing device in embodiments.

It will be further understood that there has been disclosed a portable processing device which performs processing operations as shown in FIG. 17.

Referring to FIG. 17, at step S17-2, the portable processing device determines whether a journey undertaken by a person carrying the portable processing device is an environmentally-friendly journey comprising a journey undertaken on foot or a journey undertaken using self-propelled means.

At step S17-4, the portable processing device determines a length of a said environmentally-friendly journey undertaken by the person carrying the portable processing device.

At step S17-6, the portable processing device transmits journey data to record management apparatus defining the length of an environmentally-friendly journey undertaken by the person carrying the portable processing device.

It will be further understood that an identification device for use in an environmentally-friendly vehicle has been disclosed that performs processing operations as shown in FIG. 18.

Referring to FIG. 18, at step S18-2, the identification device transmits signals identifying the vehicle as an environmentally-friendly vehicle to a portable processing device of a person in the vehicle.

Figure 19:
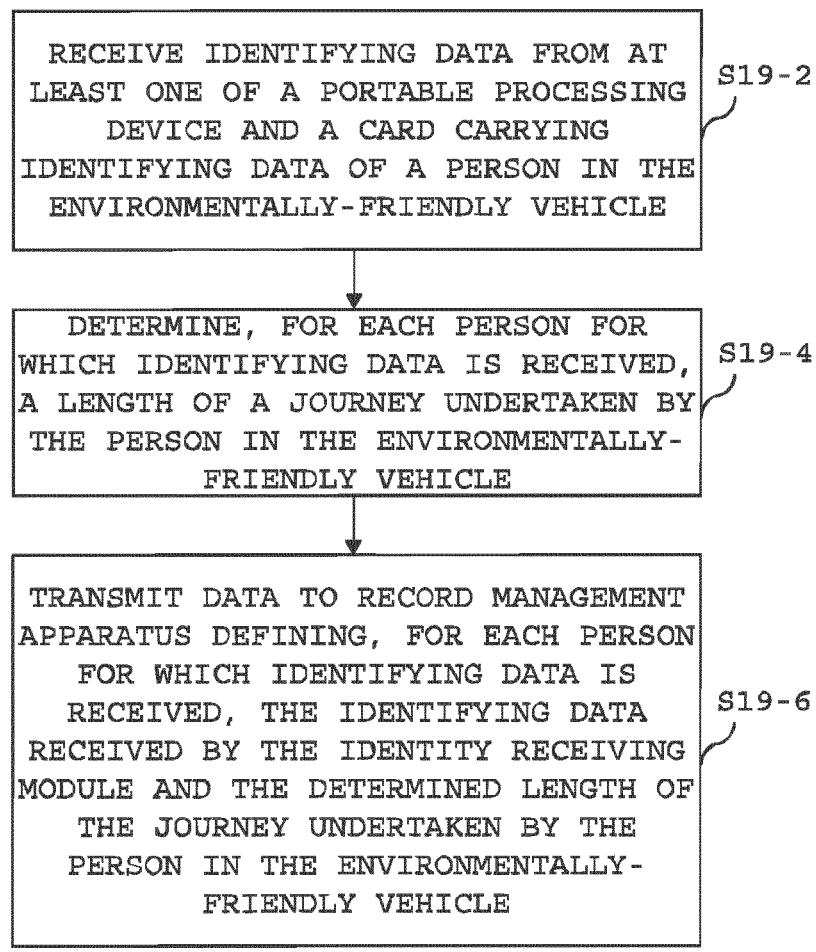
FIG. 19 shows processing operations performed by a processing device in embodiments.

It will be further understood that a processing device has been disclosed for use in an environmentally-friendly vehicle that performs processing operations as shown in FIG. 19.

Referring to FIG. 19, at step S19-2, the processing device receives identifying data from at least one of a portable processing device and a card carrying identifying data of a person in the environmentally-friendly vehicle.

At step S19-4, the processing device determines, for each person for which identifying data is received, a length of a journey undertaken by the person in the environmentally-friendly vehicle.

At step S19-6, the processing device transmits data to record management apparatus defining, for each person for which identifying data is received, the identifying data and the determined length of the journey undertaken by the person in the environmentally-friendly vehicle.

Figure 20:
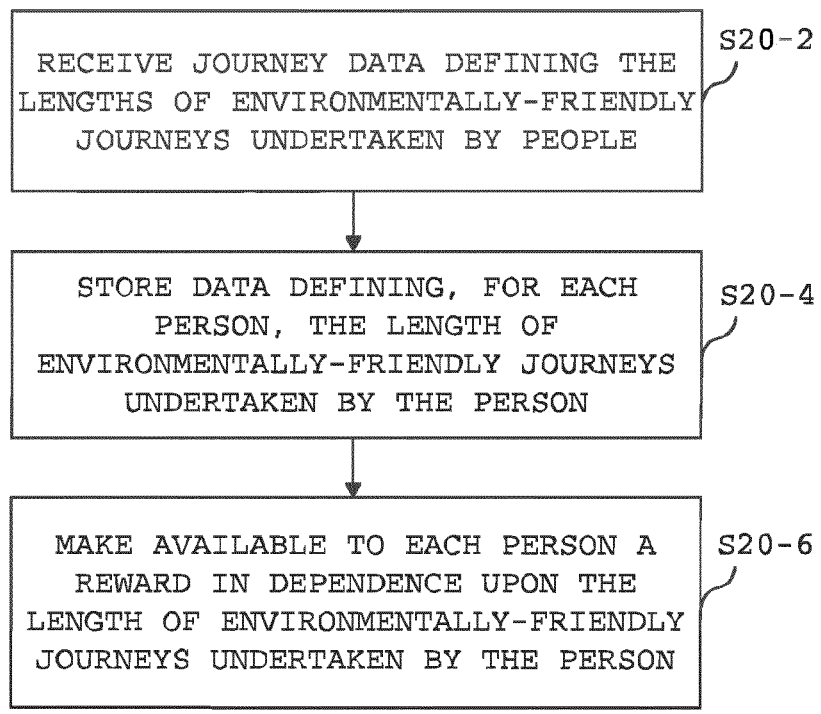
FIG. 20 shows processing operations performed by record management apparatus in embodiments.

It will be further understood that there has been disclosed a record management apparatus that performs processing operations as shown in FIG. 20.

Referring to FIG. 20, at step S20-2, the record management apparatus receives journey data defining the lengths of environmentally-friendly journeys undertaken by people.

At step S20-4, the record management apparatus stores data defining, for each person, the length of environmentally-friendly journeys undertaken by the person.

At step S20-6, the record management apparatus makes available to each person a reward in dependence upon the length of environmentally-friendly journeys undertaken by the person.

[Modifications]

Many modifications and variations can be made to the embodiments described above.

For example, in the second embodiment, processing device 1120 which works with portable processing devices 1080 of people in the environmentally-friendly vehicle and processing device 1084 which works with cards of people in the environmentally-friendly vehicle are separate processing devices. However, instead, processing devices 1120 and 1084 could be integrated, for example to form a single device.

In embodiments described above, the portable processing devices 80, 1080 are carried by people. These portable processing devices could be miniaturised and incorporated in clothing or accessories worn or carried by a person such as a coat, shirt, dress, shoes, belt, glasses, briefcase, handbag, etc.

In the embodiments described above, the determination as to whether a person is undertaking an environmentally-friendly journey comprising a journey on self-propelled means is made by the portable processing device 80, 1080 carried by the person, for example, using speed, acceleration and/or vibration data from sensors in the portable processing device. However, instead, an identification device similar to identification device 120 provided in environmentally-friendly vehicles in the first embodiment may be provided on the self-propelled means (for example a bicycle) and the portable processing device carried by the person may be configured to determine that a person is undertaking an environmentally-friendly vehicle on self-propelled means by detecting the characteristic signal from the identification device on the self-propelled means. Alternatively, a processing device 1120, 1084 as in the second embodiment may be provided on the self-propelled means and may perform processing as described above with reference to FIGS. 14 and/or FIG. 15 to determine that a person is undertaking an environmentally-friendly journey on the self-propelled means, to calculate the length of the journey, and to transmit data to the record management apparatus.

In the embodiments described above, air quality sensors may be carried not only by people, but also by environmentally-friendly vehicles and the air quality measurement data from the sensors in the environmentally-friendly vehicles transmitted to the record management apparatus. Air quality sensors may also be attached to buildings or street infrastructure (road signs) to create a further level of air quality or other data. Such sensors may be powered by ambient or other sources, such as RF harvesting.

The app in the embodiments described above could be configured to facilitate the redemption and sharing of rewards.

The app in the embodiments described above could be configured to provide motivational messages to encourage people to use environmentally-friendly transport more often and to earn more miles and rewards, and to contribute to improvements in their own environment and local area and to provide comparative data of the relative performance of streets, regions, boroughs and cities in their efforts to improve air quality through the generation and redemption of environmentally-friendly miles.

The app in the embodiments described above could be configured to enable the portable processing device on which it is loaded to become a power source for any air quality sensor(s) carried by the person. For example, this functionality would enable the portable processing device to trickle-charge an air quality sensor when the sensor is placed near to it.

In the embodiment described above, the record management apparatus makes rewards available to a person in dependence upon the lengths of environmentally-friendly journeys undertaken by the person such that when allocating the rewards, journeys in environmentally-friendly vehicles are given the same weight as journeys undertaken on foot which are also given the same weight as journeys undertaken using self-propelled means. However, different weights may be allocated to different types of environmentally-friendly journey when allocating the rewards. For example, more rewards may be allocated to the same length of environmentally-friendly journey undertaken on foot or by self-propelled means than the same length of journey undertaken in an environmentally-friendly vehicle. Similarly, more rewards may be allocated to an environmentally-friendly journey undertaken on foot than to the same length of environmentally-journey undertaken using self-propelled means.

The record management apparatus in the embodiments described above could be configured to provide promotional campaigns, such as a reward for the person who earns the most miles each month, or the borough that has the highest total of miles generated by their residents. Additionally the record management apparatus could enable the user to have a record of the total miles generated and converted into carbon credits during their lifetime membership of the scheme and hence their direct personal contribution to reducing climate change and poor air quality. The summation of these individual records by age, sex, social group, living address and other demographic indicators could provide, when aggregated and analysed, valuable information to help planners and marketing people to devise effective campaigns and/or modifications to city infrastructure and transport provisions and policies to motivate further improvements over time.

The record management apparatus and/or app in the embodiments described above could be configured to provide marketing opportunities for companies and organisations to advertise and sell environmentally-friendly goods and services, with a commission being charged on each advert and/or sale.

The record management apparatus in the embodiments described above may be configured to sell anonymised user travel and air quality measurement data to enable improved urban planning and transport pricing policies.

In addition to keeping a record of the total length of environmentally-friendly journeys undertaken by each person, the record management apparatus in the embodiments described above may be configured to calculate and provide to each person a measure of the amount of $CO_2$, PM2.5, PM10 and $NO_x$ that are not being created and released into the atmosphere as a result of the person undertaking their environmentally-friendly journeys.

A skilled person will, of course, understand that many further modifications and variations can be made without departing from the spirit and scope of the present invention.

The invention claimed is:

1. A portable processing device, comprising:
   a journey type determining module operable to determine whether a journey undertaken by a person carrying the portable processing device is an environmentally-friendly journey comprising a journey undertaken in an environmentally-friendly vehicle, a journey undertaken using self-propelled means or a journey undertaken on foot, wherein an environmentally-friendly vehicle comprises a vehicle wherein at least one of: (i) its emissions are below an environmental emissions threshold value, and (ii) at least a threshold amount of its energy comes from renewable sources, and wherein the journey type determining module is configured to detect a signal transmitted by an identification device carried in an environmentally-friendly vehicle;
   a journey length determining module operable to determine a length of a said environmentally-friendly journey undertaken by the person carrying the portable processing device, wherein for a journey undertaken in an environmentally-friendly vehicle, the journey length determining module is configured to repeatedly determine whether the journey type determining module has received a signal from a said identification device and to determine a journey length based on a duration over which the journey type determining module has received signals from said identification device; and
   a communication module operable to transmit journey data to record management apparatus defining the length of the environmentally-friendly journey undertaken by the person carrying the portable processing device.

2. A portable processing device according to claim 1, wherein the journey type determining module is operable to determine that a journey is an environmentally-friendly journey comprising a journey in an environmentally-friendly vehicle by detecting a said signal from the identification device in the environmentally-friendly vehicle.

3. A portable processing device according to claim 1, wherein:
   the signal from the identification device in the environmentally-friendly vehicle identifies at least one of the operator of the environmentally-friendly vehicle and the environmentally-friendly vehicle itself; and
   the communication module is further operable to transmit vehicle data to the record management apparatus defining at least one of the operator of the environmentally-friendly vehicle and the environmentally-friendly vehicle itself in which the environmentally-friendly journey was undertaken.

4. A portable processing device according to claim 1, wherein the journey type determining module is operable to determine whether a journey is an environmentally-friendly journey comprising a journey undertaken on foot in dependence upon at least one of speed during the journey, acceleration during the journey and vibrations during the journey.

5. A portable processing device according to claim 1, wherein the journey type determining module is operable to determine whether a journey is an environmentally-friendly journey comprising a journey undertaken using self-propelled means in dependence upon at least one of speed during the journey, acceleration during the journey and vibrations during the journey.

6. A portable processing device according to claim 1, wherein the journey type determining module is operable to determine that a journey is an environmentally-friendly journey comprising a journey using self-propelled means by detecting a signal from a device on the self-propelled means.

7. A portable processing device according to claim 1, wherein the communication module is further operable to transmit validation data for the environmentally-friendly journey to the record management apparatus, the validation data comprising at least one of position data, acceleration data and vibration data.

8. A portable processing device according to claim 1, further comprising an identity providing module operable to provide an identity of at least one of the portable processing device and the person carrying the portable processing device to said identification device in an environmentally-friendly vehicle in which the person is travelling.

9. An identification device for an environmentally-friendly vehicle, wherein an environmentally-friendly vehicle comprises a vehicle wherein at least one of: (i) its emissions are below an environmental emissions threshold value, and (ii) at least a threshold amount of its energy comes from renewable sources, the identification device comprising:
   an identity providing module operable to repeatedly transmit signals identifying the vehicle as an environmentally-friendly vehicle to a portable processing device of a person in the vehicle.

10. An identification device according to claim 9, wherein the identity providing module is further operable to transmit signals identifying at least one of the operator of the environmentally-friendly vehicle and the environmentally-friendly vehicle itself.

11. The identification device of claim 9 wherein the environmentally-friendly vehicle comprises self-propelled means.

12. A processing device for mounting in an environmentally-friendly vehicle, wherein an environmentally-friendly vehicle comprises a vehicle wherein at least one of: (i) its emissions are below an environmental emissions threshold value, and (ii) at least a threshold amount of its energy comes from renewable sources, the processing device comprising:
   an identity receiving module operable to receive identifying data from at least one of a portable processing device and a card carrying identifying data of a person in the environmentally-friendly vehicle;
   a journey length determining module operable to determine, for each person for which identifying data is received, a length of a journey undertaken by the person in the environmentally-friendly vehicle based on a duration over which the identity receiving module has received identifying data; and
   a communication module operable to transmit data to record management apparatus defining, for each person for which identifying data is received, the identifying data received by the identity receiving module and the determined length of the journey undertaken by the person in the environmentally-friendly vehicle.

13. A processing device according to claim 12, wherein the communication module is further operable to transmit data to the record management apparatus identifying at least one of the operator of the environmentally-friendly vehicle and the environmentally-friendly vehicle itself.

14. A processing device according to claim 12 wherein the environmentally-friendly vehicle comprises self-propelled means.

15. A method performed by a portable processing device, comprising:
- determining whether a journey undertaken by a person carrying the portable processing device is an environmentally-friendly journey comprising a journey undertaken in an environmentally-friendly vehicle, a journey undertaken using self-propelled means or a journey undertaken on foot, wherein an environmentally-friendly vehicle comprises a vehicle wherein at least one of: (i) its emissions are below an environmental emissions threshold value, and (ii) at least a threshold amount of its energy comes from renewable sources;
- in the event that it is determined that a journey is an environmentally-friendly journey:
- determining a length of the environmentally-friendly journey undertaken by the person carrying the portable processing device; and
- transmitting journey data to record management apparatus defining the length of the environmentally-friendly journey undertaken by the person carrying the portable processing device, wherein for a journey undertaken in an environmentally-friendly vehicle, determining the length of the journey comprises repeatedly determining whether a signal has been received from an identification device of the environmentally-friendly vehicle and determining a journey length based on a duration over which said signals have been received from said identification device.

16. A non-transitory storage medium storing computer program instructions which, when executed, cause a programmable processing apparatus to perform the method of claim 15.

17. A method performed by a processing device in an environmentally-friendly vehicle, wherein an environmentally-friendly vehicle comprises a vehicle wherein at least one of: (i) its emissions are below an environmental emissions threshold value, and (ii) at least a threshold amount of its energy comes from renewable sources, the method comprising:
- receiving identifying data from at least one of a portable processing device and a card carrying identifying data of a person in the environmentally-friendly vehicle;
- determining, for each person for which identifying data is received, a length of a journey undertaken by the person in the environmentally-friendly vehicle based on a duration over which the identity receiving module has received identifying data; and
- transmitting data to record management apparatus defining, for each person for which identifying data is received, the received identifying data and the determined length of the journey undertaken by the person in the environmentally-friendly vehicle.

18. A non-transitory storage medium storing computer program instructions which, when executed, cause a programmable processing apparatus to perform the method of claim 17.

19. The portable processing device of claim 1, wherein the portable processing device determines whether a journey undertaken by a person carrying the portable processing device is an environmentally-friendly journey comprising a journey undertaken in an environmentally-friendly vehicle by detecting a signal from said identification device that is in the environmentally-friendly vehicle.

* * * * *